(12) United States Patent
Green

(10) Patent No.: US 11,622,850 B2
(45) Date of Patent: Apr. 11, 2023

(54) INTRAOCULAR LENSES AND PERIPHERAL PORTION STABILIZATION

(71) Applicant: Alcon Inc., Fribourg (CH)

(72) Inventor: George Green, Belmont, CA (US)

(73) Assignee: Alcon Inc., Fribourg (CH)

(*) Notice: Subject to any disclaimer, the term of this patent is extended or adjusted under 35 U.S.C. 154(b) by 0 days.

(21) Appl. No.: 16/758,341

(22) PCT Filed: Oct. 30, 2018

(86) PCT No.: PCT/US2018/058108
§ 371 (c)(1),
(2) Date: Apr. 22, 2020

(87) PCT Pub. No.: WO2019/089515
PCT Pub. Date: May 9, 2019

(65) Prior Publication Data
US 2020/0337833 A1  Oct. 29, 2020

Related U.S. Application Data

(60) Provisional application No. 62/580,210, filed on Nov. 1, 2017.

(51) Int. Cl.
*A61F 2/16* (2006.01)

(52) U.S. Cl.
CPC .......... *A61F 2/16* (2013.01); *A61F 2002/169* (2015.04); *A61F 2002/16901* (2015.04); *A61F 2250/0003* (2013.01); *A61F 2250/0036* (2013.01)

(58) Field of Classification Search
CPC .................. A61F 2/16; A61F 2002/169; A61F 2002/16901
See application file for complete search history.

(56) References Cited

U.S. PATENT DOCUMENTS

| | | | |
|---|---|---|---|
| 4,118,808 A | 10/1978 | Poler | |
| 6,200,342 B1 | 3/2001 | Tassignon | |
| 6,881,225 B2 | 4/2005 | Okada | |
| 7,217,288 B2 | 5/2007 | Esch et al. | |
| 8,603,165 B2 | 12/2013 | Park | |
| 2007/0100444 A1 | 5/2007 | Brady et al. | |
| 2009/0306774 A1 | 12/2009 | Park | |
| 2010/0179653 A1 | 7/2010 | Argento et al. | |
| 2011/0208301 A1 | 8/2011 | Anvar et al. | |

(Continued)

FOREIGN PATENT DOCUMENTS

| | | |
|---|---|---|
| CN | 107205814 | 5/2019 |
| RU | 2602224 | 11/2016 |

(Continued)

*Primary Examiner* — Leslie Lopez
(74) *Attorney, Agent, or Firm* — Levine Bagade Han LLP

(57) ABSTRACT

An intraocular lens, wherein an outer periphery of an optic portion has a peripheral surface, and a radially inner portion of a peripheral portion of the IOL has an inner surface, wherein the peripheral surface is directly adjacent to the inner surface, and wherein the peripheral surface does not directly extend (coupled to or integrally formed therewith) from the inner surface, and wherein the peripheral surface and the inner surface are configured so that the peripheral portion is stabilized in at least one of, and optionally both of, the proximal and distal directions relative to the optic portion.

20 Claims, 21 Drawing Sheets

(56) References Cited

U.S. PATENT DOCUMENTS

2013/0131794 A1* 5/2013 Smiley ................ A61F 2/1613
623/6.37
2017/0049561 A1   2/2017 Smiley et al.
2017/0181850 A1   6/2017 De Juan, Jr. et al.

FOREIGN PATENT DOCUMENTS

| WO | WO-2015148673 A1 * | 10/2015 | ........... A61F 9/0026 |
| WO | WO 2016/201351 | 12/2016 | |
| WO | WO 2017/079733 | 5/2017 | |
| WO | WO 2017/096087 | 6/2017 | |
| WO | WO 2019/089515 | 5/2019 | |

* cited by examiner

Section A-A

_US 11,622,850 B2_

INTRAOCULAR LENSES AND PERIPHERAL PORTION STABILIZATION

CROSS REFERENCE TO RELATED APPLICATIONS

This application is a U.S. national application filed under 35 U.S.C. 371 to PCT International Application No. PCT/US2018/058108, filed Oct. 30, 2018, which claims priority to U.S. Prov. App. No. 62/580,210, filed Nov. 1, 2017, each of which is incorporated by reference herein in its entirety.

This application incorporates by reference herein PCT Publication No. WO 2017/079733 A1, published May 11, 2017.

INCORPORATION BY REFERENCE

All publications and patent applications mentioned in this specification are herein incorporated by reference to the same extent as if each individual publication or patent application was specifically and individually indicated to be incorporated by reference.

BACKGROUND

Intraocular lenses may include one or more peripheral portions that are disposed further radially outward than an optic portion. During the surgical implantation procedure, at least a portion of the IOL may receive out of plane forces in the anterior-to-posterior direction, which may make it more difficult to achieve planar placement of the intraocular lens during at least a portion of the surgical procedure.

SUMMARY OF THE DISCLOSURE

One aspect of the disclosure is an intraocular lens ("IOL"), wherein an outer periphery of an optic portion has a peripheral surface, and a radially inner portion of a peripheral non-optic portion of the IOL has an inner surface, wherein the peripheral surface is directly adjacent to the inner surface, and wherein the peripheral surface does not directly extend (not coupled to and not integrally formed therewith) from the inner surface, and wherein the peripheral surface and the inner surface are both configured so that the peripheral portion and the optic portion are stabilized relative to one another in at least one of, and optionally both of, the proximal and distal directions where the peripheral surface is directly adjacent to the inner surface.

The optic peripheral surface may comprises a depression, and wherein at least a portion of the inner surface can be disposed in the depression.

The optic peripheral surface and the inner surface of the peripheral portion can be directly adjacent at a location that is spaced away from and around the optic periphery from a location where the peripheral portion extends from (e.g., coupled to or formed integrally with) the optic portion.

DETAILED DESCRIPTION

The disclosure relates generally to intraocular lenses. In some embodiments the intraocular lenses described herein are adapted to be positioned within a native capsular bag in which a native lens has been removed. In these embodiments a peripheral non-optic portion (i.e., a portion not specifically adapted to focus light on the retina) is adapted to respond to capsular bag reshaping due to ciliary muscle relaxation and contraction. The response is a deformation of the peripheral portion that causes a fluid to be moved between the peripheral portion and an optic portion to change an optical parameter (e.g., power) of the intraocular lens.

Figure 1A:
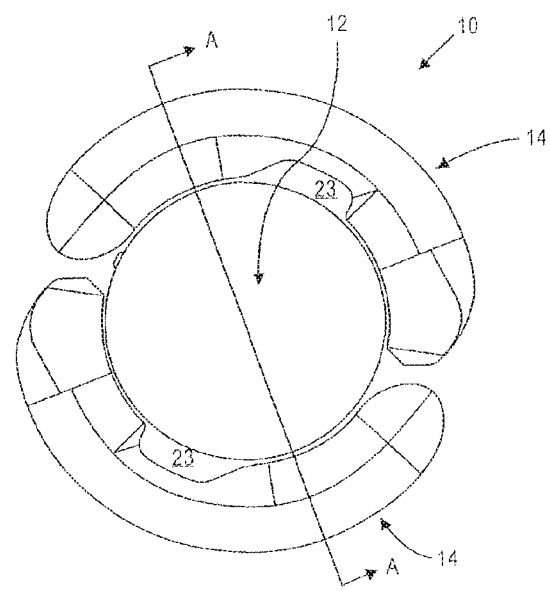
FIGS. 1A and 1B illustrate an exemplary accommodating intraocular lens.
Figure 1B:
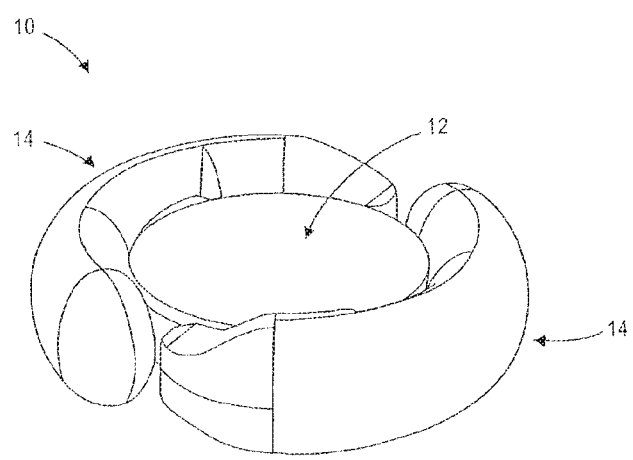

FIG. 1A is a top view illustrating accommodating intraocular lens 10 that includes optic portion 12 and a peripheral portion that in this embodiment includes first and second haptics 14 coupled to and extending peripherally from optic portion 12. Optic portion 12 is adapted to refract light that enters the eye onto the retina. Haptics 14 are configured to engage a capsular bag and are adapted to deform in response to ciliary muscle related capsular bag reshaping. FIG. 1B is a perspective view of intraocular lens 10 showing optic portion 12 and haptics 14 coupled to optic portion 12.

The haptics are in fluid communication with the optic portion. Each haptic has a fluid chamber that is in fluid communication with an optic chamber in the optic portion. The haptics are formed of a deformable material and are adapted to engage the capsular bag and deform in response to ciliary muscle related capsular bag reshaping. When the haptics deform the volume of the haptic fluid chamber changes, causing a fluid disposed in the haptic fluid chambers and the optic fluid chamber to either move into the optic fluid chamber from the haptic fluid chambers, or into the haptic fluid chambers from the optic fluid chamber. When the volume of the haptic fluid chambers decreases, the fluid is moved into the optic fluid chamber. When the volume of the haptic fluid chamber increases, fluid is moved into the haptic fluid chambers from the optic fluid chamber. The fluid flow into and out of the optic fluid chamber changes the configuration of the optic portion and the power of the intraocular lens.

Figure 1C:
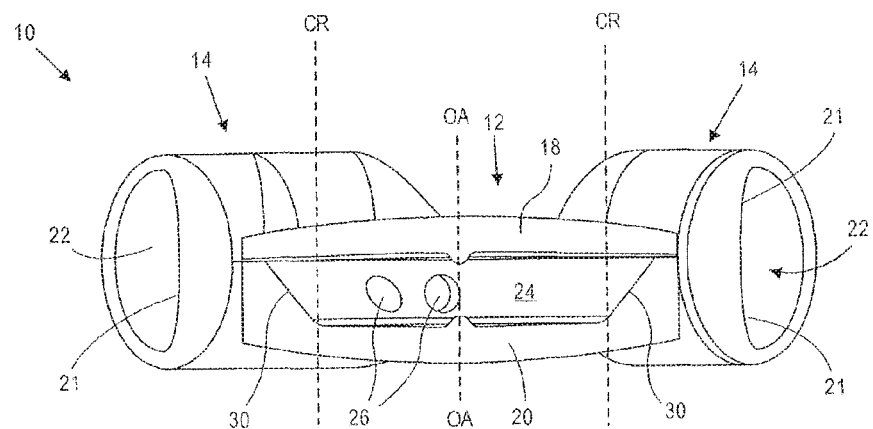
FIG. 1C illustrates a sectional view of the accommodating intraocular lens from FIGS. 1A and 1B.

FIG. 1C is a side sectional view through Section A-A indicated in FIG. 1A. Optic portion 12 includes deformable anterior element 18 secured to deformable posterior element 20. Each haptic 14 includes a fluid chamber 22 that is in fluid communication with optic fluid chamber 24 in optic portion 12. Only the coupling between the haptic 14 to the left in the figure and option portion 12 is shown (although obscured) in the sectional view of FIG. 1C. The haptic fluid chamber 22 to the left in the figure is shown in fluid communication with optic fluid chamber 24 via two apertures 26, which are formed in posterior element 20. The haptic 14 to the right in FIG. 1C is in fluid communication with optic chamber 24 via two additional apertures also formed in posterior element (not shown) substantially 180 degrees from the apertures shown.

Figure 1D:
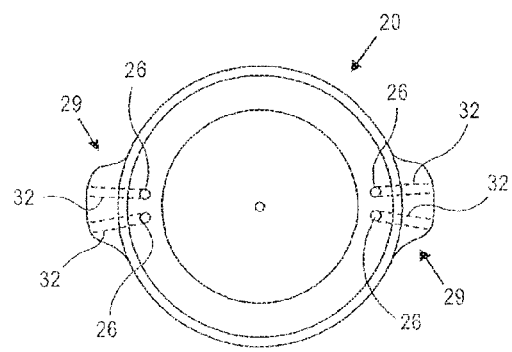
FIG. 1D is a top view of an exemplary posterior element of an accommodating intraocular lens.

FIG. 1D is a top view of posterior element 20 (anterior element 18 and haptics 14 not shown). Posterior element 20 includes buttress portions 29 in which channels 32 are formed. Channels 32 provide fluid communication between optic portion 12 and haptics 14. Apertures 26 are disposed at one end of channels 32. The optic fluid chamber 24 is therefore in fluid communication with a single haptic via two fluid channels. Buttress portions 29 are configured and sized to be disposed within an opening formed in haptics 14 that defines one end of the haptic fluid chamber, as described below. Each of buttress portions 29 includes two channels formed therein. A first channel in a first buttress is in alignment with a first channel in the second buttress. The second channel in the first buttress is in alignment with the second channel in the second buttress.

There are exemplary advantages to having two channels in each buttress as opposed to one channel. A design with two channels rather than one channel helps maintain dimensional stability during assembly, which can be important when assembling flexible and thin components. Additionally, it was observed through experimentation that some one-channel designs may not provide adequate optical quality throughout the range of accommodation. In particular, lens astigmatism may occur in some one-channel designs, particularly as the intraocular lens accommodated. It was discovered that the two-channel buttress designs described herein can help reduced astigmatism or the likelihood of astigmatism, particularly as the lens accommodated. Astigmatism is reduced in these embodiments because the stiffness of the buttress is increased by the rib portion between the two channels. The additional stiffness results in less deflection due to pressure changes in the channels. Less deflection due to the pressure changes in the channels results in less astigmatism. In some embodiments the channels are between about 0.4 mm and about 0.6 mm in diameter. In some embodiments the channels are about 0.5 mm in diameter. In some embodiments the distance between the apertures is about 0.1 mm to about 1.0 mm.

Figure 1E:
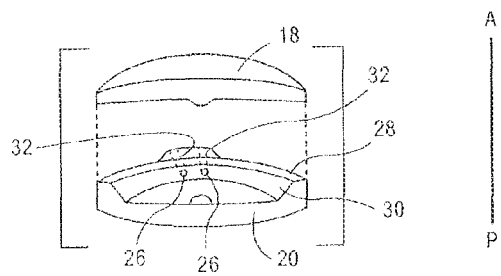
FIG. 1E is a sectional assembly view of an exemplary optic onion of an accommodating intraocular lens.

FIG. 1E is a side assembly view through section A-A of optic portion 12, which includes anterior element 18 and posterior element 20 (haptics not shown for clarity). By including fluid channels 32 in posterior element 20, posterior element 20 needs to have enough structure through which the channels 32 can be formed. Buttress portions 29 provide that structures in which channels 32 can be formed. At its peripheral-most portion posterior element 20 is taller than anterior element 18 in the anterior-to-posterior direction. In alternative embodiments, the channels can be formed in anterior element 18 rather than posterior element 20. The anterior element would include buttress portions 29 or other similar structure to provide structure in which the channels can be formed. In these alternative embodiments the posterior element could be formed similarly to anterior element 18.

As shown in FIG. 1E, posterior element 20 is secured to anterior element 18 at peripheral surface 28, which extends around the periphery of posterior element 20 and is a flat surface. Elements 18 and 20 can be secured together using known biocompatible adhesives. Anterior element 18 and posterior element 20 can also be formed from one material to eliminate the need to secure two elements together. In some embodiments the diameter of the region at which anterior element 18 and posterior element 20 are secured to one another is about 5.4 mm to about 6 mm in diameter.

In some embodiments the thickness of anterior element 18 (measured in the anterior-to-posterior direction) is greater along the optical axis ("OA" in FIG. 1C) than at the periphery. In some embodiments the thickness increases continuously from the periphery towards the thickest portion along the optical axis.

In some embodiments the thickness of posterior element 20 decreases from the location along the optical axis towards the edge of central region "CR" identified in FIG. 1C. The thickness increases again radially outward of central region CR towards the periphery, as can be seen in FIG. 1C. In some particular embodiments central region CR is about 3.75 mm in diameter. The apertures are formed in beveled surface 30.

In some embodiments the thickness of posterior element 20 along the optical axis is between about 0.45 mm and about 0.55 mm and the thickness at the periphery of posterior element 20 is between about 1.0 mm and about 1.3.

In some embodiments the thickness of posterior element 20 along the optical axis is about 0.5 mm and the thickness at the periphery of posterior element 20 is about 1.14 mm.

In some embodiments the thickness of anterior element 18 along the optical axis is between about 0.45 mm to about 0.55 mm, and in some embodiments is between about 0.50 mm to about 0.52 mm. In some embodiments the thickness at the periphery of anterior element 18 is between about 0.15 mm and about 0.4 mm, and in some embodiments is between about 0.19 mm and about 0.38 mm.

In one particular embodiment the thickness of anterior element 18 along the optical axis is about 0.52 mm and the thickness of the periphery of anterior element 18 is about 0.38 mm, and the thickness of posterior element 20 along the optical axis is about 0.5 mm and the thickness at the periphery of posterior element 20 is about 1.14 mm.

In one particular embodiment the thickness of anterior element 18 along the optical axis is about 0.5 mm and the thickness of the periphery of anterior element 18 is about 0.3 mm, and the thickness of posterior element 20 along the optical axis is about 0.5 mm and the thickness at the periphery of posterior element 20 is about 1.14 mm.

In one particular embodiment the thickness of anterior element 18 along the optical axis is about 0.51 mm and the thickness of the periphery of anterior element 18 is about 0.24 mm, and the thickness of posterior element 20 along the optical axis is about 0.5 mm and the thickness at the periphery of posterior element 20 is about 1.14 mm.

In one particular embodiment the thickness of anterior element 18 along the optical axis is about 0.52 mm and the thickness of the periphery of anterior element 18 is about 0.19 mm, and the thickness of posterior element 20 along the optical axis is about 0.5 mm and the thickness at the periphery of posterior element 20 is about 1.14 mm.

The optic portion is adapted to maintain optical quality throughout accommodation. This ensures that as the accommodating intraocular lens transitions between the dis-accommodated and accommodated configurations, the optic portion maintains optical quality. A number of factors contribute to this beneficial feature of the accommodating intraocular lenses herein. These factors include the peripheral region at which anterior element 18 is secured to posterior element 20, the shape profile of the anterior element 18 and posterior element 20 inside central region CR of the optic portion (see FIG. 1C), and the thickness profiles of anterior element 18 and posterior element 20. These contributing factors ensure that both the anterior and posterior elements flex in such a way as to maintain the shape necessary to maintain optical quality across a range of optical powers.

Figure 1F:
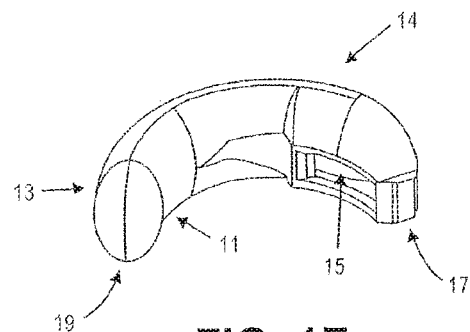
FIGS. 1F and 1G illustrate an exemplary haptic.

FIG. 1F illustrates one haptic 14 from intraocular lens 10 (optic portion 12 and the second haptic not shown for clarity). Haptic 14 includes radially outer portion 13 adapted to face the direction of the zonules, and radially inner portion 11, which faces the periphery of the optic (not shown). Haptic 14 includes a first end region 17 which is secured to optic portion 12, and second end region 19 that is closed. Haptic 14 also includes opening 15 in first end region 17 that provides the fluid communication with the haptic. In this embodiment opening 15 is sized and configured to receive buttress portion 29 of optic portion 12 therein.

Figure 1G:
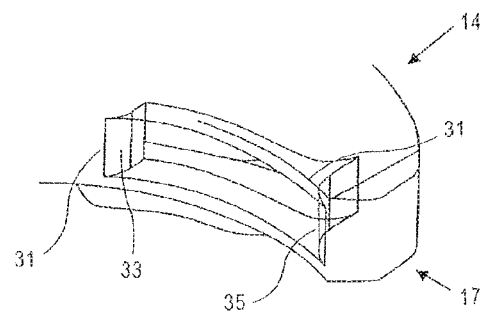

FIG. 1G is a close up view of opening 15 in haptic 14, which is adapted to receive buttress portion 29 therein. The opening 15 has curved surfaces 33 and 35 that are shaped to mate with curved surfaces on the optic buttress 29. Surface 31 surrounds opening 15 and provides a surface to which a corresponding surface of the optic can be secured.

Figure 1H:
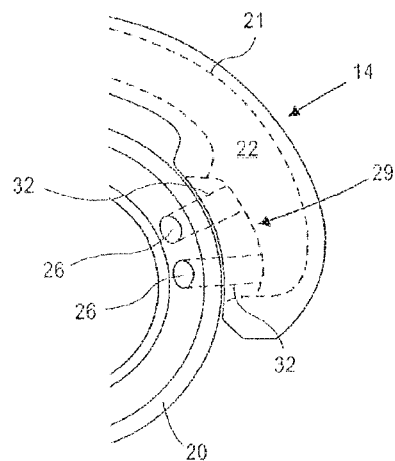
FIG. 1H illustrate an exemplary coupling between an optic portion and a haptic.

FIG. 1H is a top close up view of buttress portion 29 (in phantom) from posterior element 20 disposed within opening 15 in haptic 14 (anterior element of the optic not shown for clarity). Channels 32 are shown in phantom. Haptic 14 includes fluid chamber 22 defined by inner surface 21. Fluid moves between the optic fluid chamber and haptic fluid chamber 22 through channels 32 upon the deformation of haptic 14.

Figure 2A:
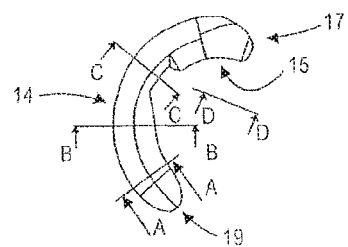
FIGS. 2A, 2B, and 2C illustrate an exemplary haptic.
Figure 2B:
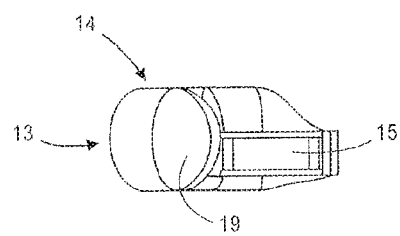
Figure 2C:
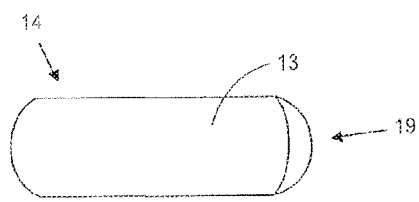

FIG. 2A is a top view showing one haptic 14 shown in FIGS. 1A-1H. The optic portion and the second haptic are not shown. Four sections A-D are identified through the haptic. FIG. 2B illustrates a side view of haptic 14, showing opening 15 and closed end 19. FIG. 2C is a side view of haptic 14 showing radially outer portion 13 and closed end 19.

Figure 2D:
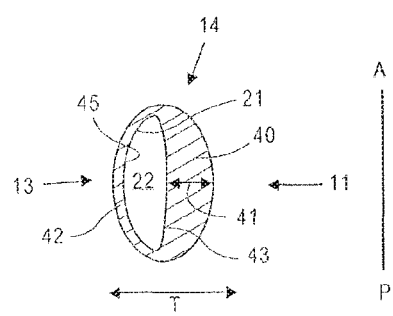
FIGS. 2D, 2E, and 2F illustrate sectional views of the haptic from FIG. 2A.

FIG. 2D is the cross sectional view through section A-A shown in FIG. 2A. Of the four sections shown in FIG. 2A, section A-A is the section closest to closed end 19. Radially inner portion 11 and radially outer portion 13 are identified. Fluid channel 22 defined by surface 21 is also shown. In this section the radially inner portion 40 is radially thicker (in the direction "T") than radially outer portion 42. Inner portion 40 provides the haptic's stiffness in the anterior-to-posterior direction that more predictably reshapes the capsule in the anterior-to-posterior direction. Radially inner portion 40 has a greatest thickness dimension 41, which is along an axis of symmetry in this cross section. The outer surface of haptic 14 has a generally elliptical configuration in which the greatest height dimension, in the anterior-to-posterior direction ("A-P"), is greater than the greatest thickness dimension (measured in the "T" dimension). The fluid chamber 22 has a general D-shaped configuration, in which the radially inner wall 43 is less curved (but not perfectly linear) than radial outer wall 45. Radially outer portion 42 engages the capsular bag where the zonules attach thereto, whereas the thicker radially portion 40 is disposed adjacent the optic.

Figure 2E:
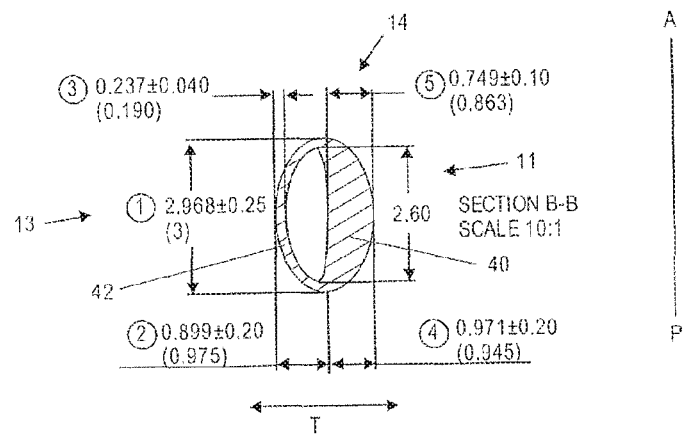

FIG. 2E illustrates section B-B shown in FIG. 2A. Section B-B is substantially the same as section A-A, and FIG. 2E provides exemplary dimensions for both sections. Radially inner portion 40 has a greatest thickness along the midline of about 0.75 mm (in the radial direction "T"). Radially outer portion 42 has a thickness along the midline of about 0.24 mm. Fluid chamber 22 has a thickness of about 0.88 mm. Haptic 14 has a thickness along the midline of about 1.87 mm. The height of the haptic in the anterior to posterior dimension is about 2.97 mm. The height of the fluid chamber is about 2.60 mm. In this embodiment the thickness of the radially inner portion 40 is about 3 times the thickness of the radially outer portion 42. In some embodiments the thickness of the radially inner portion 40 is about 2 times the thickness of the radially outer portion 42. In some embodiments the thickness of the radially inner portion 40 is about 2 to about 3 times the thickness of the radially outer portion 42. In some embodiments the thickness of the radially inner portion 40 is about 1 to about 2 times the thickness of the radially outer portion 42.

Fluid chamber 22 is disposed in the radially outer portion of haptic 14. Substantially the entire radially inner region of haptic 14 in this section is bulk material. Since the fluid chamber 22 is defined by surfaces 43 and 45 (see FIG. 2D), the positioning and size of fluid chamber 22 depends on the thickness of the radially inner portion 40 and the radially outer portion 42.

Figure 2F:
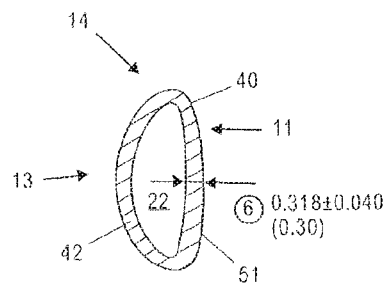

FIG. 2F illustrates Section C-C shown in FIG. 1A. In Section C-C radially inner portion 40 is not as thick as radially inner portion 40 in sections A-A and B-B, although in Section C-C radially inner portion 40 is slightly thicker than radially outer portion 42. In this particular embodiment radially inner portion 40 is about 0.32 mm in Section C-C. Radially outer portion 42 has a thickness about the same as the radially outer thickness in Sections A-A and B-B, about 0.24 mm. The outer surface of haptic 14 does not have the same configuration as the outer surface in Sections A-A and Section B-B. In Section C-C the radially inner outer surface of haptic 51 is more linear than in Sections A-A and Section B-B, giving the outer surface of haptic in Section C-C a general D-shape. In Section C-C fluid chamber 22 has a general D-shape, as in Sections A-A and Section B-B. The haptic, in Section C-C has a fluid chamber configuration that is substantially the same as the fluid chamber configurations in Sections A-A and B-B, but has an outer surface with a configuration different than the configuration of the outer surface of haptic 14 in Sections A-A and B-B.

The thinner radially inner portion 40 in Section C-C also creates access pathways 23 that are shown in FIG. 1A. This space between optic portion 12 and haptics 14 allows a physician to insert one or more irrigation and/or aspiration devices into space 23 during the procedure and apply suction to remove viscoelastic fluid that may be used in the delivery of the intraocular lens into the eye. The pathways 23 could also be anywhere along the length of the haptic, and there could be more than one pathway 23. This application incorporates by reference the disclosure in FIGS. 23 and 24, and the textual description thereof, from U.S. Pub. No. 2008/0306588, which include a plurality of pathways in the haptics.

Figure 2G:
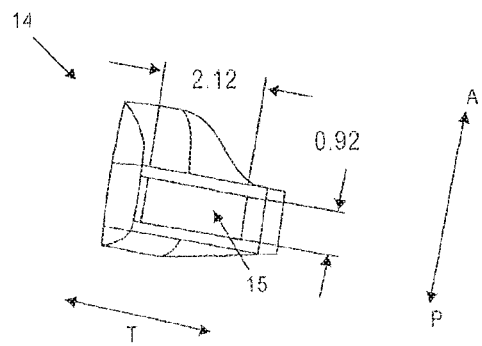
FIG. 2G illustrates an opening in a first end of the haptic from FIGS. 2A-2C.

FIG. 2G shows a view through Section D-D from FIG. 2A. Haptic 14 includes opening 15 therein, which is adapted to receive the buttress from the optic portion as described herein. The height of opening 15 in this embodiment is about 0.92 mm. The width, or thickness, of the opening is about 2.12 mm.

Figure 3:
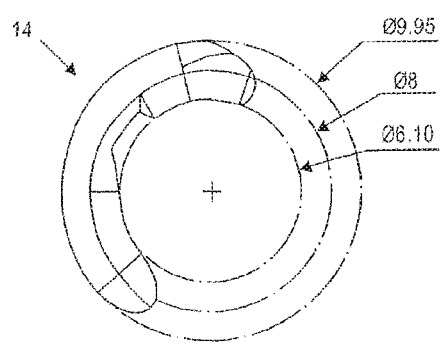
FIG. 3 illustrates exemplary diameters of an accommodating intraocular lens.

FIG. 3 illustrates relative diameters of optic portion 12 (not shown) and of the peripheral portion, which includes two haptics 14 (only one haptic is shown). In this embodiment the optic has a diameter of about 6.1 cm, while the entire accommodating intraocular lens, including the peripheral portion, has a diameter of about 9.95 cm. The dimensions provided are not intended to be strictly limiting.

Figure 4:
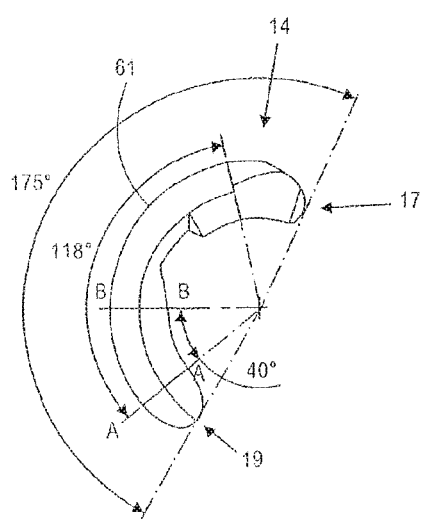
FIG. 4 illustrates an exemplary haptic.

FIG. 4 is a top view of haptic 14, showing that haptic 14 subtends an angle of about 175 degrees around optic (i.e., substantially 180 degrees). The optic portion is not shown for clarity. The two haptics therefore each subtend an angle of about 180 degrees around the optic. A first region 61 of haptic 14 is shown to subtend exemplary angle of about 118 degrees. This is the radially outermost portion of haptic 14, is adapted to engage the capsular bag, and is adapted to be most responsive to capsular shape changes. Region 61 can be thought of as the most responsive part of haptic 14.

The angle between Sections A-A and B-B, which are considered the boundaries of the stiffer radially inner portion of the haptic, is about 40 degrees. The stiff radially inner portion of haptic 14 is positioned directly adjacent the periphery of the optic. The dimensions and angles provided are not intended to be strictly limiting.

Figure 5A:
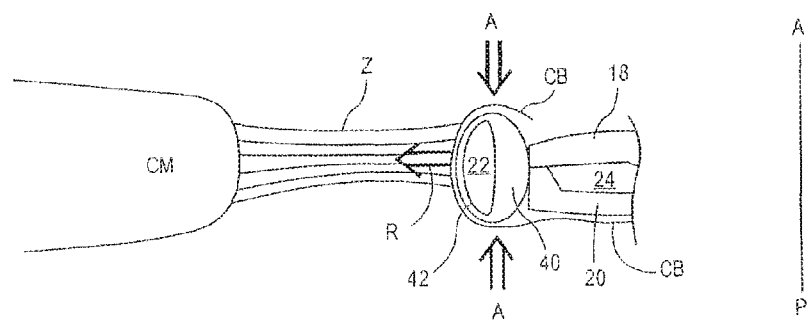
FIGS. 5A and 5B illustrate the deformation of an exemplary haptic in response to exemplary forces.
Figure 5B:
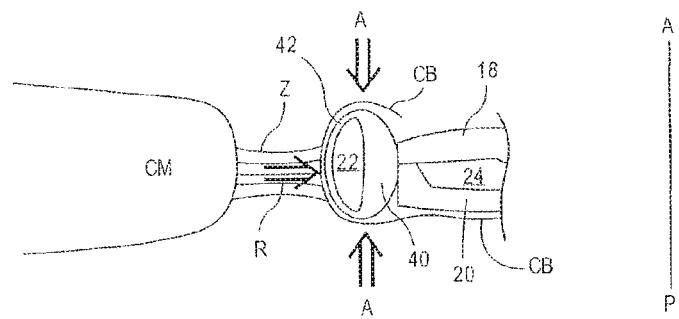

FIGS. 5A and 5B illustrate a portion of accommodating intraocular lens 10 positioned in a capsular bag ("CB") after a native lens has been removed from the CB. The anterior direction is on top and the posterior direction is on bottom in each figure. FIG. 5A shows the accommodating intraocular lens in a lower power, or dis-accommodated, configuration relative to the high power, or accommodated, configuration shown in FIG. 5B.

The elastic capsular bag "CB" is connected to zonules "Z," which are connected to ciliary muscles "CM." When the ciliary muscles relax, as shown in FIG. 5A, the zonules are stretched. This stretching pulls the capsular bag in the generally radially outward direction due to radially outward forces "R" due to the general equatorial connection location between the capsular bag and the zonules. The zonular stretching causes a general elongation and thinning of the capsular bag. When the native lens is still present in the capsular bag, the native lens becomes flatter (in the anterior-to-posterior direction) and taller in the radial direction, which gives the lens less power. Relaxation of the ciliary muscle, as shown in FIG. 5A, provides for distance vision. When the ciliary muscles contract, however, as occurs when the eye is attempting to focus on near objects, the radially inner portion of the muscles move radially inward, causing the zonules to slacken. This is illustrated in FIG. 5B. The slack in the zonules allows the capsular bag to move towards a generally more curved configuration in which the anterior surface has greater curvature than in the disaccommodated configuration, providing higher power and allowing the eye to focus on near objects. This is generally referred to as "accommodation," and the lens is said to be in an "accommodated" configuration.

In section A-A (which is the same as section B-B) of haptic 14, illustrated in FIGS. 5A and 5B, radially inner portion 40 includes thicker bulk material that provides haptic 14 with stiffness in the anterior-to-posterior direction. When capsular bag forces are applied to the haptic in the anterior-to-posterior direction, the inner portion 40, due to its stiffness, deforms in a more repeatable and predictable manner making the base state of the lens more predictable. Additionally, the haptic, due to its stiffer inner portion, deforms the capsule in a repeatable way in the anterior-to-posterior direction. Additionally, because the haptic is less flexible along the length of the haptic, the accommodating intraocular lens's base state is more predictable because bending along the length of the haptic is one way in which fluid can be moved into the optic (and thereby changing the power of the lens). Additional advantages realized with the stiffer inner portion are that the haptics are stiffer to other forces such as torqueing and splaying because of the extra bulk in the inner portion.

The radially outer portion 42 is the portion of the haptic that directly engages the portion of the capsular bag that is connected to the zonules. Outer portion 42 of the haptics is adapted to respond to capsular reshaping forces "R" that are applied generally radially when the zonules relax and stretch. This allows the haptic to deform in response to ciliary muscle related forces (i.e., capsular contraction and relaxation) so that fluid will flow between the haptic and the optic in response to ciliary muscle relaxation and contraction. This is illustrated in FIG. 5B. When the ciliary muscles contract (FIG. 5B), the peripheral region of the elastic capsular bag reshapes and applies radially inward forces "R" on radially outer portion 42 of haptic 14. The radially outer portion 42 is adapted to deform in response to this capsular reshaping. The deformation decreases the volume of fluid channel 22, which forces fluid from haptic chamber 22 into optic chamber 24. This increases the fluid pressure in optic chamber 42. The increase in fluid pressure causes flexible anterior element 18 and flexible posterior element 20 to deform, increasing in curvature, and thus increasing the power of the intraocular lens.

The haptic is adapted to be stiffer in the anterior-to-posterior direction than in the radial direction. In this embodiment the radially outer portion 42 of haptic 14 is more flexible (i.e., less stiff) in the radial direction than the stiffer inner portion 40 is in the anterior-to-posterior direction. This is due to the relative thicknesses of outer portion 42 and inner portion 40. The haptic is thus adapted to deform less in response to forces in the anterior-to-posterior direction than to forces in the radial direction. This also causes less fluid to be moved from the haptic into the optic in response to forces in the anterior-to-posterior direction than is moved into the optic in response to forces in the radial direction. The haptic will also deform in a more predictable and repeatable manner due to its stiffer radially inner portion.

The peripheral portion is thus more sensitive to capsular bag reshaping in the radial direction than to capsular bag reshaping in the anterior-to-posterior direction. The haptics are adapted to deform to a greater extent radially than they are in the anterior-to-posterior direction. The disclosure herein therefore includes a peripheral portion that is less sensitive to capsular forces along a first axis, but is more sensitive to forces along a second axis. In the example above, the peripheral portion is less sensitive along the posterior-to-anterior axis, and is more sensitive in the radial axis.

An exemplary benefit of the peripheral portions described above is that they deform the capsular bag in a repeatable way and yet maintain a high degree of sensitivity to radial forces during accommodation. The peripheral portions described above are stiffer in the anterior-to-posterior direction than in the radial direction.

An additional example of capsular forces in the anterior-to-posterior direction is capsular forces on the peripheral portion after the accommodating intraocular lens is positioned in the capsular bag, and after the capsular bag generally undergoes a healing response. The healing response generally causes contraction forces on the haptic in the anterior-to-posterior direction, identified in FIG. 5A by forces "A." These and other post-implant, such as non-accommodating-related, capsular bag reshaping forces are described in U.S. application Ser. No. 12/685,531, filed Jan. 11, 2010, which is incorporated herein by reference. For example, there is some patient to patient variation in capsular bag size, as is also described in detail in U.S. application Ser. No. 12/685,531, filed Jan. 11, 2010. When an intraocular lens is positioned within a capsular bag, size differences between the capsule and intraocular lens may cause forces to be exerted on one or more portions of the intraocular lens in the anterior-to-posterior direction.

In the example of capsular healing forces in the anterior-to-posterior direction, the forces may be able to deform a deformable haptic before any accommodation occurs. This deformation changes the volume of the haptic fluid chamber, causing fluid to flow between the optic fluid chamber and the haptic fluid chambers. This can, in some instances undesirably, shift the base power of the lens. For example, fluid can be forced into the optic upon capsular healing, increasing the power of the accommodating intraocular lens, and creating a permanent myopic shift for the accommodating intraocular lens. Fluid could also be forced out of the optic and into the haptics, decreasing the power of the accommodating intraocular lens.

As used herein, "radial" need not be limited to exactly orthogonal to the anterior-to-posterior plane, but includes planes that are 45 degrees from the anterior-to-posterior plane.

Exemplary fluids are described in U.S. application Ser. No. 12/685,531, filed Jan. 11, 2010, and in U.S. application Ser. No. 13/033,474, filed Feb. 23, 2011, both of which are incorporated herein by reference. For example, the fluid can be a silicone oil that is or is not index-matched with the polymeric materials of the anterior and posterior elements. When using a fluid that is index matched with the bulk material of the optic portion, the entire optic portion acts a single lens whose outer curvature changes with increases and decreases in fluid pressure in the optic portion.

In the embodiment in FIGS. 2A-2G above the haptic is a deformable polymeric material that has a substantially uniform composition in Sections A-A, B-B, and C-C. The stiffer radially inner body portion 40 is attributed to its thickness. In alternative embodiments the radially inner body portion has a different composition that the outer body portion, wherein the radially inner body portion material is stiffer than the material of the radially outer body portion. In these alternative embodiments the thicknesses of the radially inner and outer portions can be the same.

Figure 6:
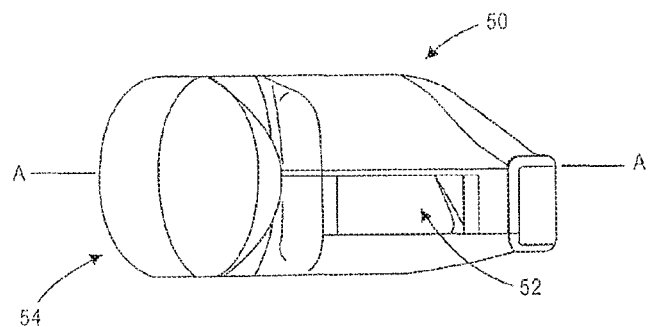
FIG. 6 illustrates an exemplary fluid opening in an exemplary haptic.

FIG. 6 illustrates haptic 50, which is the same haptic configuration as in shown in FIG. 2B. The radially outer portion 54 is identified. The haptic has axis "A" halfway through the height of the haptic, or alternatively stated, axis A passes through the midpoint of the height of the haptic in the anterior-to-posterior direction. Opening 52, in which the optic buttress is disposed, is on the posterior side of axis A. In this embodiment the optic sits slightly closer to the posterior-most portion of the haptics than the anterior-most portion of the haptics. That is, in this embodiment the optic is not centered with the haptics in the anterior-to-posterior direction.

Figure 7:
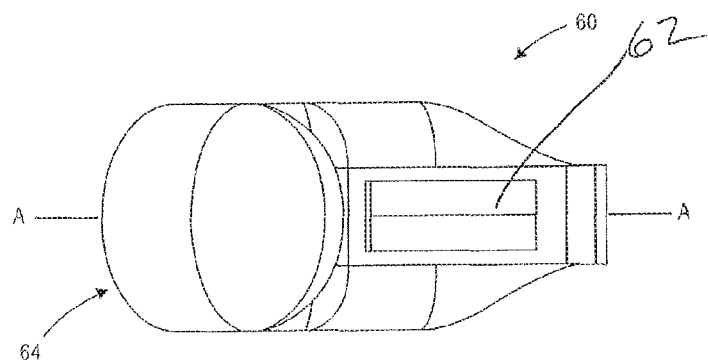
FIG. 7 illustrates an exemplary fluid opening in an exemplary haptic.
Figure 8:
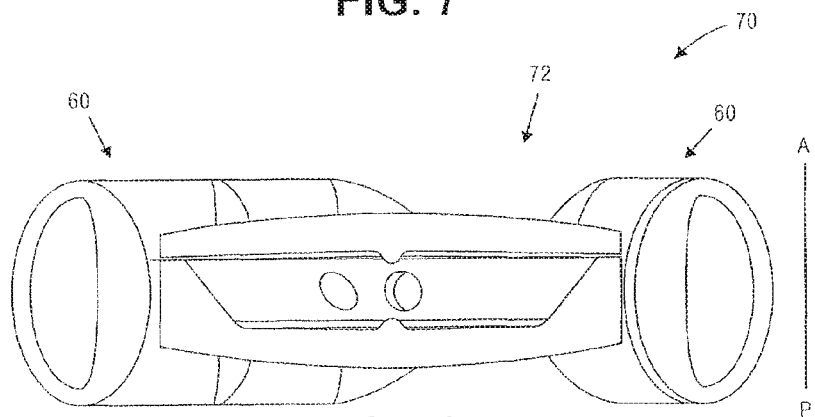
FIG. 8 illustrates a sectional view of an exemplary accommodating intraocular lens.

FIG. 7 illustrates an alternative haptic 60 (optic not shown), wherein the radially outer portion 64 is identified. Haptic 60 includes axis "A" halfway through the thickness of the haptic, or alternatively stated, axis A passes through the midpoint of the height of the haptic in the anterior-to-posterior direction. Opening 62 is symmetrical about the axis A, and an axis passing through the midpoint of opening 62 is aligned with axis A. Additionally, axis A is an axis of symmetry for haptic 60. The symmetry of the haptic along axis A can improve the ability to mold low relatively low stress components. FIG. 8 shows an embodiment of intraocular lens 70 in which the optic 72 is coupled to two haptics 60, which are the haptics shown in FIG. 7. The optic sits further in the anterior direction that in the embodiment in which the opening is not along the midline of the haptic. In this embodiment, optic 72 is centered, in the anterior-to-posterior direction, with the haptics. The cross sections A-A, B-B, and C-C of haptic 60 are the same as those shown in other embodiments shown above, but the haptics can have any alternative configuration as well.

Figure 9:
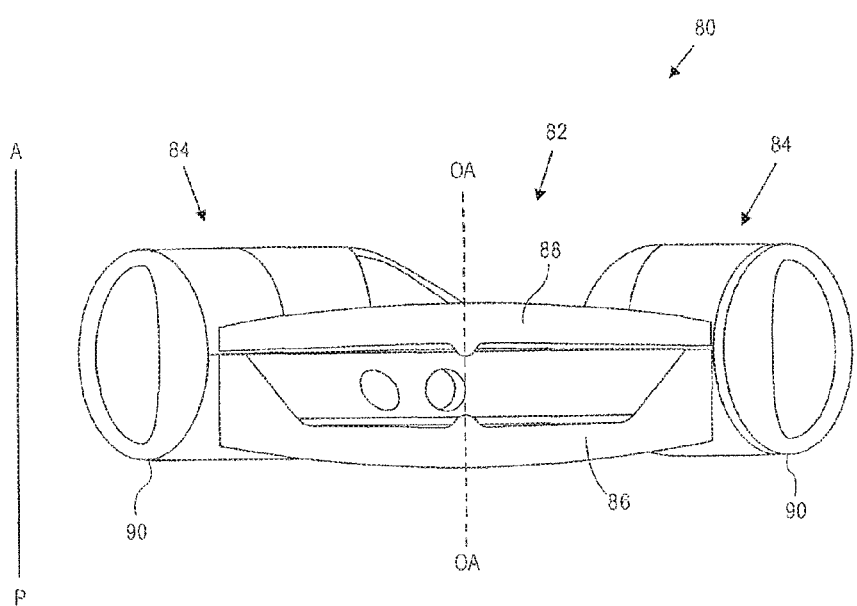
FIG. 9 illustrates a sectional view of an exemplary accommodating intraocular lens with relatively short haptics.

FIG. 9 illustrates intraocular lens 80 including optic 82 and two haptics 84. The optic is the same as the optic portions described herein. Haptics 84 are not as tall, measured in the anterior-to-posterior direction, as haptic 60, haptic 50, or haptic 14. In exemplary embodiments haptics 84 are between about 2.0 mm and about 3.5 mm tall, and in some embodiments they are about 2.8 mm tall. Intraocular lens 80 can be considered a size "small" accommodating intraocular lens for patients with a capsular bag that is below a certain threshold size. The posterior surface of posterior element 86 is disposed slightly further in the posterior direction than the posterior-most portions 90 of haptics 84.

Figure 10:
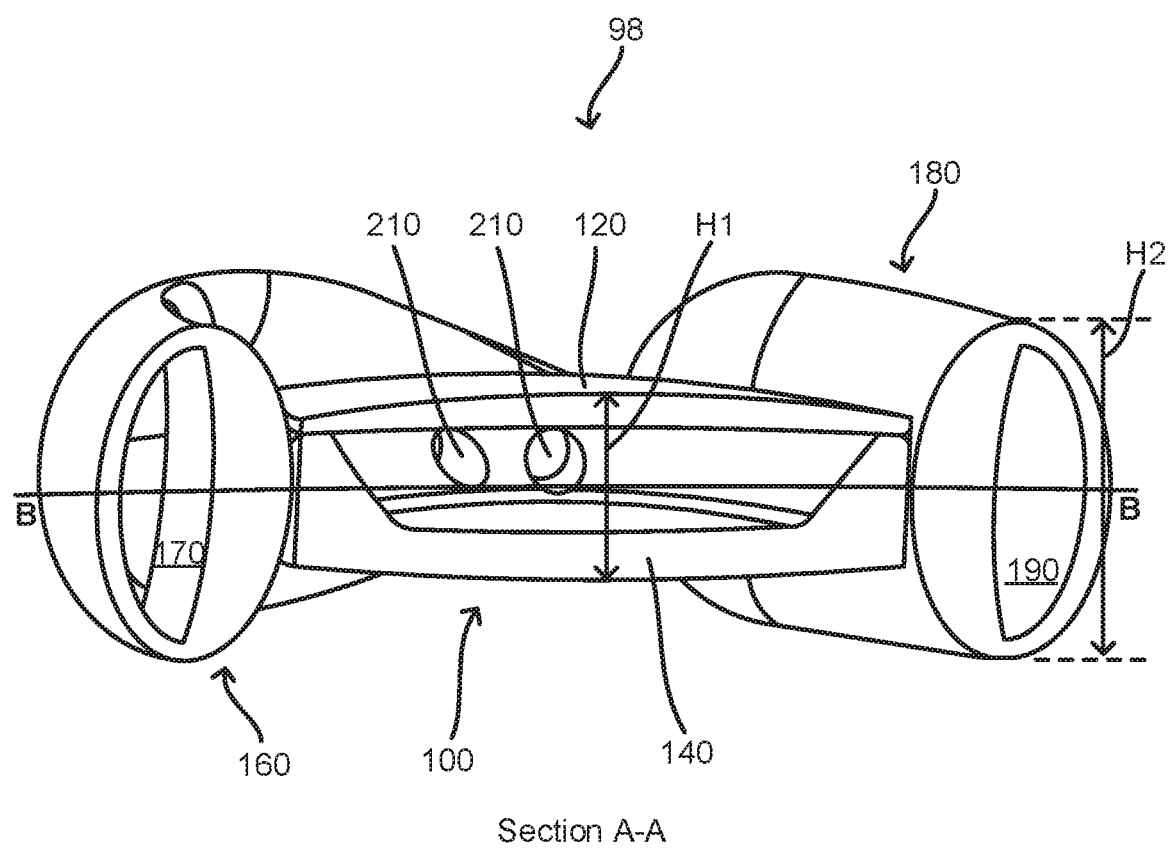
FIG. 10 illustrate a sectional view of an exemplary accommodating intraocular lens with an optic centered with a peripheral portion.

FIG. 10 illustrates an accommodating intraocular lens 98 that includes an optic body 100 and a peripheral non-optic body, which in this embodiment includes haptics 160 and 180. Optic body 100 can be in fluid communication with one or both haptics 160 and 180, and fluid movement between the optic and haptics in response to ciliary muscle movement can change the power of the intraocular lens. This general process of fluid-driven accommodation in response to deformation of the haptics can be found herein. Optic 100 includes anterior element 120 secured to posterior element 140, together defining an optic fluid chamber in communication with haptic fluid chambers 170 and 190 in the haptics. The "height" of the components in this disclosure is measured in the anterior-to-posterior direction. Optic 100 has a greatest height "H1" dimension measured in the anterior to posterior direction along the optic axis. Haptics 160 and 180 have greatest height "H2" dimensions measured in the anterior to posterior direction parallel to the optical axis. The optic body has a centerline B, measured perpendicular to the optical axis and passing through the midpoint of H1. The haptics also have centerlines, B, measured perpendicular to the optical axis and passing through the midpoint of H2. In this embodiment the centerlines coincide and are the same centerline B. Stated alternatively, the anterior-most surface or point of anterior element 120 is spaced from the anterior-most point or surface of the haptics the same distance as is the posterior-most surface or point of posterior element 140 from the posterior-most point or surface of the haptics. They can be considered substantially the same lines in some embodiments even if they do not coincide, but are near in space to one another (e.g., a few millimeters away). An optic centered with the haptics is also shown in FIG. 8.

In this embodiment the position of the optic 100 relative to the haptics can provide some benefits. For example, during folding and/or insertion, the centered (or substantially centered) optic, measured in the anterior-to-posterior direction, can prevent or reduce the likelihood of one or more haptics from folding over the anterior element 120 or posterior element 140, which may happen when the optic body is not substantially centered relative to the haptics. For example, an optic that is much closer to the posterior side of the lens may increase the likelihood that a haptic (e.g., a haptic free end) can fold over the anterior surface of the optic during deformation, loading, or implantation.

An additional benefit to having the optic body 100 centered or substantially centered relative to the peripheral body is that is it easier for the optic to pass through the capsulorhexis when placed in the eye. When the optic is closer to the posterior side of the lens, it may be more difficult for it to rotate into the capsular bag.

An additional benefit is that, compared to optics that are further in the posterior direction, glare from the intraocular lens is reduced. By moving the optic in the anterior direction (it will be closer to the iris once implanted), less light can reflect off of the radially outer peripheral edge of the optic (i.e., the edge surface adjacent the haptics), thus reducing glare from edge effect.

In some embodiments of the intraocular lens in FIG. 10, anterior element 120 can have a height between 0.2 mm and 0.35 mm, such as between 0.25 mm and 0.30 mm, such as about 0.28 mm, and the posterior element 140 can have a height between 0.36 mm and 0.50 mm, such as between 0.40 mm and 0.45 mm, such as about 0.43 mm.

Prior to insertion, such as during manufacturing, the intraocular lens shown in FIG. 10 can be filled with fluid. In some embodiments the intraocular lens has a base state (at zero fluid pressure in the optic; or no fluid inside it) less than 15 D, such as about 13 D. About 13 D, as used herein, refers to base states about 10 D to about 15 D. By having a base state of about 13 D, it may be possible to generally only have to change the fluid pressure in one direction—higher. When the base state of an intraocular lens is higher, such as about 20 D, it may be necessary to change the fluid pressure either higher or lower, depending on the desired vision correction and the intended use of the intraocular lens. By having a lower base state, the changes to the state of the lens become more predictable by only having to change the base state in one direction.

One aspect of this disclosure is an accommodating intraocular lens, optionally fluid-filled and fluid-driven, that has an aspheric optical surface after manufacture and prior to implantation. That is, the intraocular lens is manufactured with an aspheric optical surface. An aspheric optical surface can avoid spherical aberration when the pupil is fully dilated. There can be challenges in manufacturing an intraocular lens, particularly an accommodating, fluid-driven intraocular lens, with aspheric optical surfaces.

In some embodiments the accommodating intraocular lens is manufactured with an aspheric anterior surface and/or an aspheric posterior surface. One exemplary manner in which a fluid-filled accommodating intraocular lens can have an anterior or posterior optical surface with built-in asphericity is to, during manufacturing, create the optical surface with a spherical configuration prior to fluid filling, then create the asphericity in the optical surface during the fill process. For example, during manufacture, one or both of the anterior surface and the posterior surface can be manufactured to have spherical outer optical surfaces. The anterior surface can then be secured to the posterior surface. One or more haptics can then be secured to the optic. In some embodiments the optic is manufactured, but prior to filling, to have a base state (at zero fluid pressure in the optic; or no fluid inside it) less than 15 D, such as about 13 D. About 13 D, as used herein, refers to base states about 10 D to about 15 D. When a fluid is injected into the accommodating intraocular lens (e.g., via a septum), the fluid filling step can increase the fluid pressure in the optic and cause the anterior surface and/or the posterior surface of the optic to have an aspherical configuration. One aspect of this disclosure is thus a method of manufacturing an accommodating intraocular lens that includes creating an optic with a fluid-filled state prior to insertion, which has asphericity built into one or more optical surfaces, such as an anterior optic surface. The method of manufacturing can include manufacturing the optic wherein the optical surface is spherical prior to fluid filling.

It may be desirable to maintain good optical quality in at least one surface of the central portion of the optic as it is deformed, either throughout disaccommodation or throughout accommodation. One of the aspects of the disclosure is an optic that has a very controlled and somewhat stable amount of asphericity in a central region of the optic, across the whole range of powers. This may be referred to herein as "beneficial asphericity" in a central region of the optic. The beneficial asphericity includes lens surfaces with surface aberrations that are configured to compensate for the spherical aberrations in the optical system of the eye, and contribute to maintaining optical quality. The beneficial asphericity is maintained across all or substantially all of the range of powers during accommodation and disaccommodation. In some instances the asphericity can be controlled such that the spherical aberration of the whole lens systems can remain low (or zero) across all range of power. The optic region outside of the central region may have larger, more uncontrolled amount of asphericity.

In some embodiments the central region of the optic, or the region of beneficial asphericity, has a diameter of less than 6.5 mm, less than 6.0 mm, less than 5.5 mm, less than 5.0 mm, less than 4.5 mm, less than 4.0 mm, less than 3.5 mm, or even less than 3.0 mm. In some embodiments the central region has a diameter between 3.5 mm and 5.5 mm. In some embodiments the central region of the optic with beneficial asphericity has a diameter less than 90% of the diameter of the optic body, less than 85%, less than 80%, or less than 75%. The diameter of the optic can be between 4 mm and 8 mm, such as between 5 mm and 7 mm. In some embodiments the central region is between 4 mm and 5 mm, and the optic diameter is between 5 mm and 7 mm. In some embodiments the central region is between 4.25 mm and 4.75 mm, and the optic diameter is between 5.75 mm and 6.25 mm.

The configuration of the anterior element and the posterior element can influence the configurations that they assume throughout deformation, either throughout accommodation or disaccommodation. In some embodiments, one or both of the anterior element and the posterior element is contoured, or configured, such that the central region of the optic has the beneficial asphericity that is controlled and beneficial to the overall system of the eye. In this embodiment anterior element 120, and to a lesser extent posterior element 140, are configured so that an anterior surface of anterior element 120 and a posterior surface of posterior element 140 maintain the controlled, beneficial asphericity in a central region of the optic during accommodation. In this embodiment one aspect of the configuration that contributes to the central portion maintaining beneficial asphericity is that anterior element 120, and optionally the posterior element 140, has a thickness (also referred to as "height" herein) that is greater in the center (such as at the apex of the anterior element 120) than at the periphery of the anterior element 120. An additional aspect of the configuration that contributes to beneficial asphericity is that the anterior element is flatter on the inner surface (posterior surface) than on the outer surface (anterior surface). During accommodation, the central region of the anterior element 120 steepens in the center (which increases power of the AIOL), but the optic body maintains its beneficial asphericity, due at least in part to the relatively larger thickness of the anterior element central region. It may also be aspherical prior to accommodating in the exemplary embodiments in which asphericity is built into the anterior element, described below.

The thickness contours of the anterior and posterior elements can contribute to the optic maintaining the beneficial asphericity across all powers, an example of which is the thickness of the anterior and posterior elements.

Figure 11:
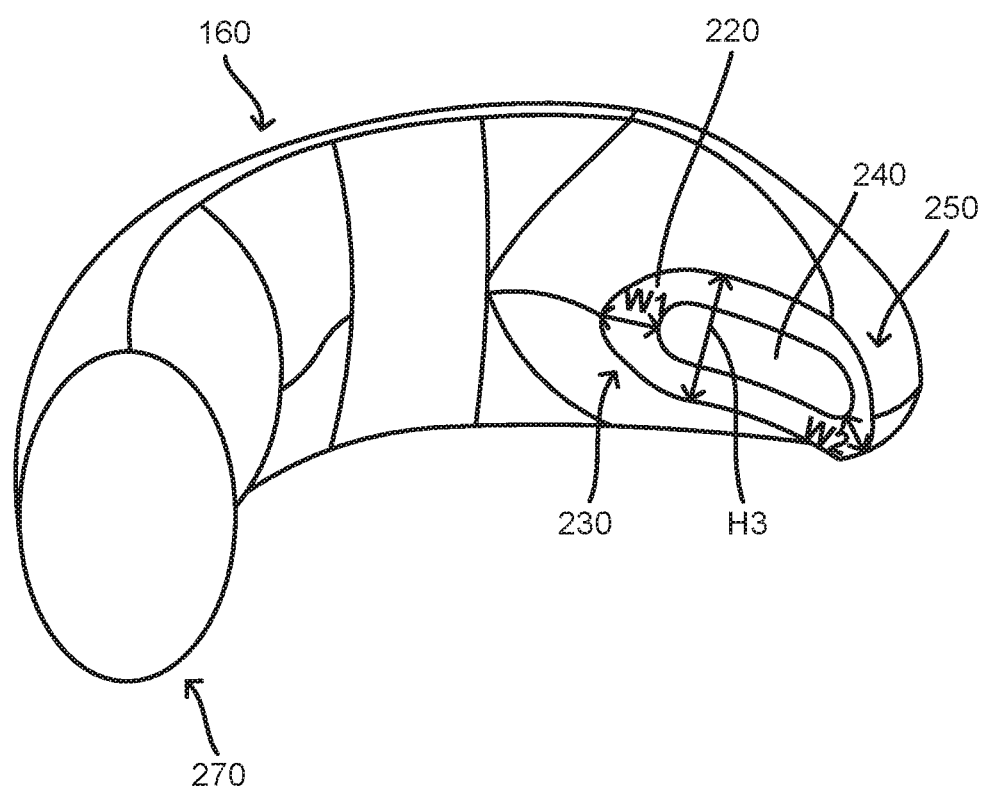
FIG. 11 is an exemplary haptic.

FIG. 11 illustrates an exemplary haptic that can be part of any of the accommodating intraocular lenses herein or other suitable IOLs not described herein. One or both haptics can be configured as shown in FIG. 11. The haptic in FIG. 11 is labeled as "160," but it is understood that the haptic in FIG. 11 can be a part of intraocular lenses other than that shown in FIG. 10. The haptic includes a surface 220 that is secured to an outer edge of the optic body. Surface 220 is a radially inner surface of the haptic, and is configured with a slight curve to it (along the length of the haptic) that is substantially the same curve as the outer edge of the optic so that the entire surface 220 interfaces the optic body outer edge surface(s). Surface 220 has a configuration relative to the optic such that an extension of the surface does not pass through an optic axis of the optic. An adhesive can be used to secure surface 220 to the optic outer edge surface(s). In this embodiment the coupling between the haptic and the optic body does not include one of the haptic and optic being disposed within a channel, bore, or aperture in the other, as can be used for some haptic/optic coupling designs, such as in the embodiment shown in FIGS. 1A-9. Some exemplary advantages of this type of design are described below.

Figure 12:
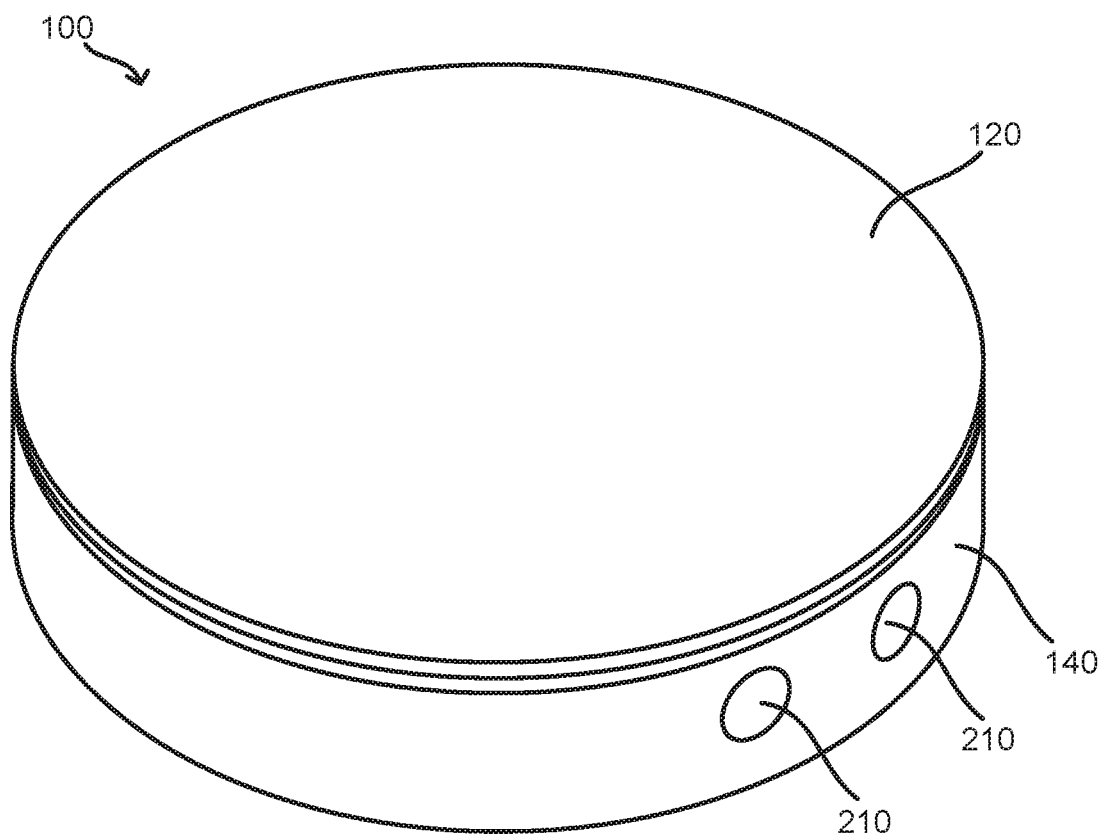
FIG. 12 shows an exemplary optic portion.

FIG. 12 shows a perspective view of optic 100, with the haptics excluded for clarity. Surface 220 of the haptic (not shown) is secured to both anterior element 120 and posterior element 140 of the optic body 100. Most of surface 220 interfaces posterior portion 140, but a portion of surface 220 interfaces anterior element 120. This is because the outer edge of the optic body is largely comprised of the posterior element 140. With different optic configurations, surface 220 could be secured to more of the anterior element than the posterior element. It is also noted that the height H3 of surface 220 (see FIG. 11) is substantially the same as the height of the outer edge of the optic body.

Figure 13:
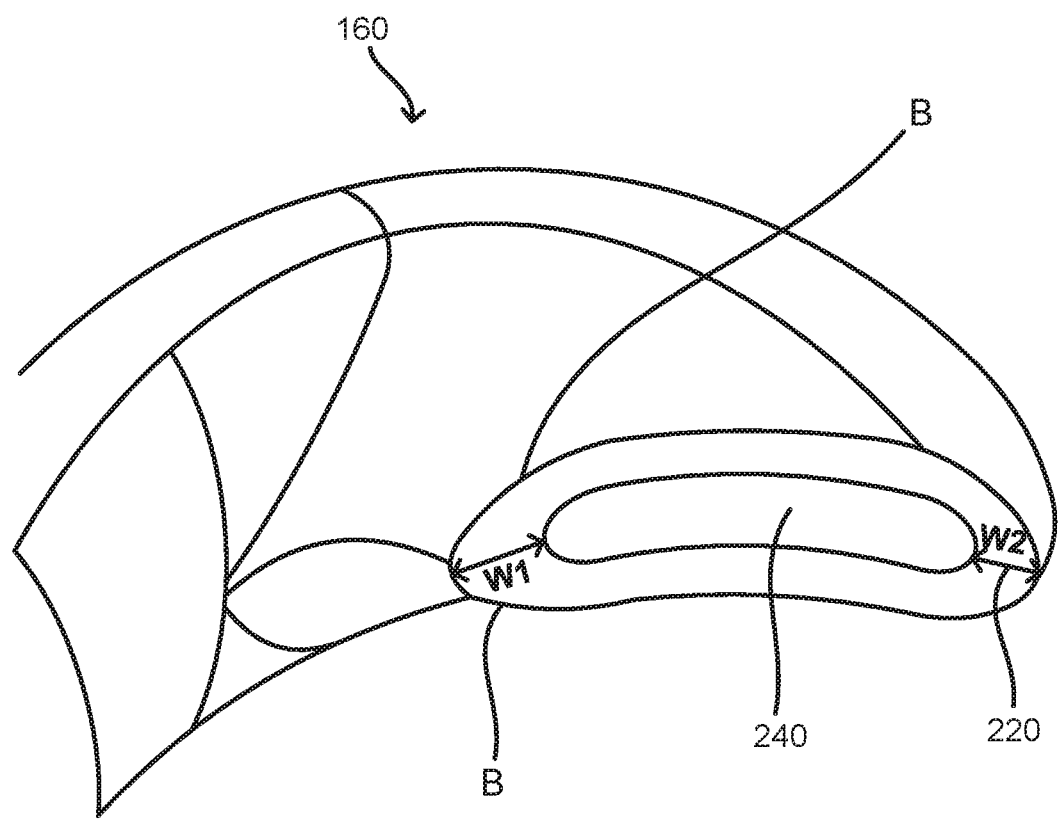
FIG. 13 shows a portion of an exemplary haptic.

Haptic 160 surface 220 has a first end region 230 (see FIG. 11) that has a configuration with a larger surface than second end region 250. End region 230 of surface 220 has a larger surface area than end region 250 of surface 220, and includes at least partially beveled surfaces B, as shown in FIG. 13. The width W1 of end region 230 is greater than width W2 of end region 250. The configuration of end region 230 can provide exemplary benefits. For example, as part of a process of loading the intraocular lens into a delivery device and/or into an eye of a patient, one or both of haptics 160 and 180 may be "splayed" relative to optic. That is, one or both haptics can be reconfigured from the natural at rest configuration shown in FIGS. 10-14 by moving free end 170 of haptic away from the optic body. The extent to which the free end (and a large portion of the haptic) is moved away from the optic during splaying can vary. In some methods of loading, one of both haptics can be splayed substantially, such that the haptic is oriented behind or in front of the optic. In some instances the haptic free end (i.e., the end of the haptic not coupled directly to the optic) is "pointing" substantially 180 degrees from where it is pointing in the at-rest configuration. In general, splaying the haptic(s) causes stresses at the coupling interface between the haptic and optic. The coupling interface between the optic and haptic must be able to withstand these forces so that the haptic does not disengage from the optic. When splaying haptics, there can be a high stress location at the optic/haptic coupling at the end of the interface 230, which is closer to the free end. End region 230 is thus the location where the haptic/optic interface is most likely to fail. End region 230, with its larger surface area and tapering and beveled configuration, acts to distribute the applying stresses (or stresses anytime haptic is reoriented relative to the optic) and prevent the haptic from disengaging from the optic.

The configuration of surface 220 can be modified in many ways to provide the desired joinery between the haptic and the optic. Joining the haptic and the optic in this manner (as opposed to having one component fit within the other) thus allows for many more interface configurations, which provides more flexibility in design.

In the embodiment of the haptic in FIG. 11, fluid aperture 240 is centered along the midline of the haptic. The centerline is defined in the same manner as described in FIG. 10. The centerline passes through the midpoint of the haptic height (measured in an anterior-to-posterior direction) in a side view of the haptic.

Other aspects of the haptic can be the same as described herein, such as a thicker radially inner wall thickness along a portion of the haptic, and one or both haptics that follows the curvature of the periphery of the optic from the coupled end to the free end, and the anterior most aspect of the haptic extending further anteriorly than the anterior-most aspect of the optic.

The posterior element 140 has two fluid channels 210 therein that are in fluid communication with the haptic fluid chambers 170 and 190. The outer edge of the posterior element 140 includes two apertures therein that define ends of the fluid channels 210. The haptic/optic interface (which can be a glue joint) surrounds the two fluid apertures in the posterior element 140. In some alternatives the optic only has one fluid channel instead of two.

FIG. 13 is another view of haptic 160, showing the slight curvature of optic interface surface 220 and fluid aperture 240 therein.

Figure 14:
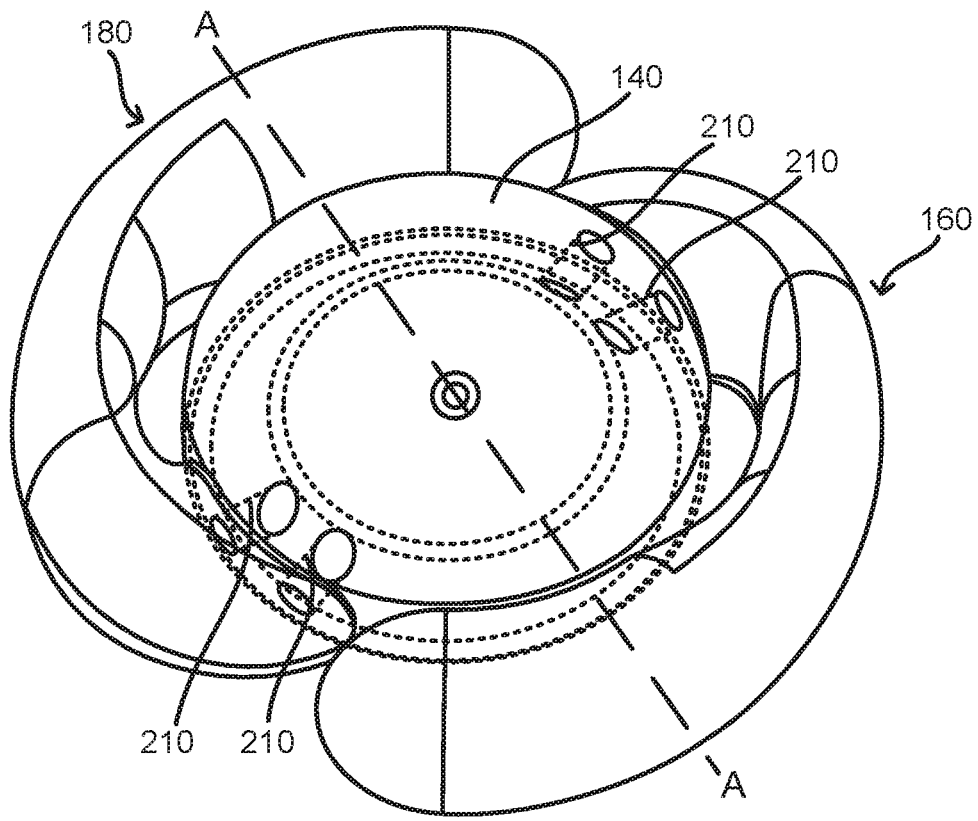
FIG. 14 shows an exemplary IOL.

FIG. 14 is a perspective view of the intraocular lens from FIG. 10, viewed from the posterior side. Fluid channels 210 can be seen in the posterior element 140, two of which are associated with each haptic. The interface between the haptics and optic can also be seen. FIG. 14 shows section A-A that is shown in FIG. 10.

Figure 15:
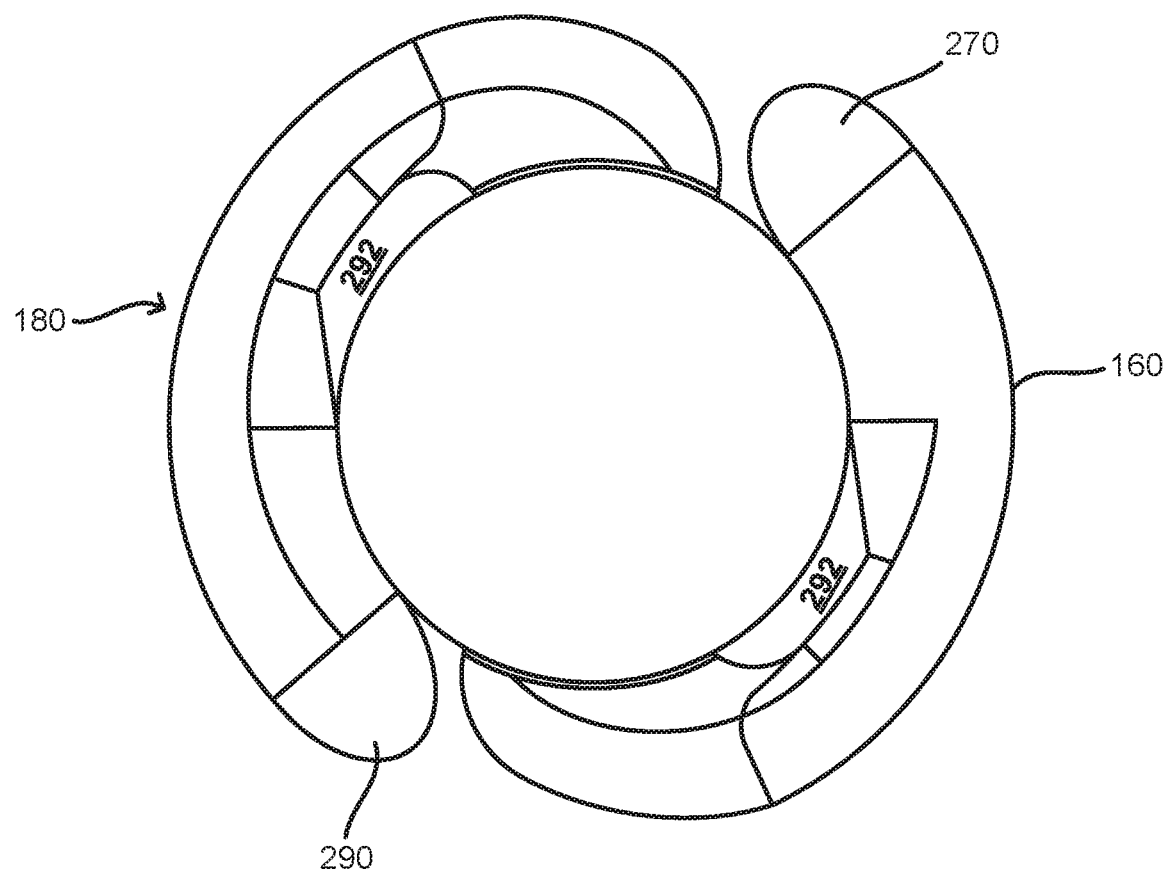
FIG. 15 shows an exemplary IOL.

FIG. 15 shows an additional view of the intraocular lens from FIG. 10, in which spacings 292 between the outer edge of optic and haptics can be seen, as well as the coupling between the optic and haptics.

Figure 16:
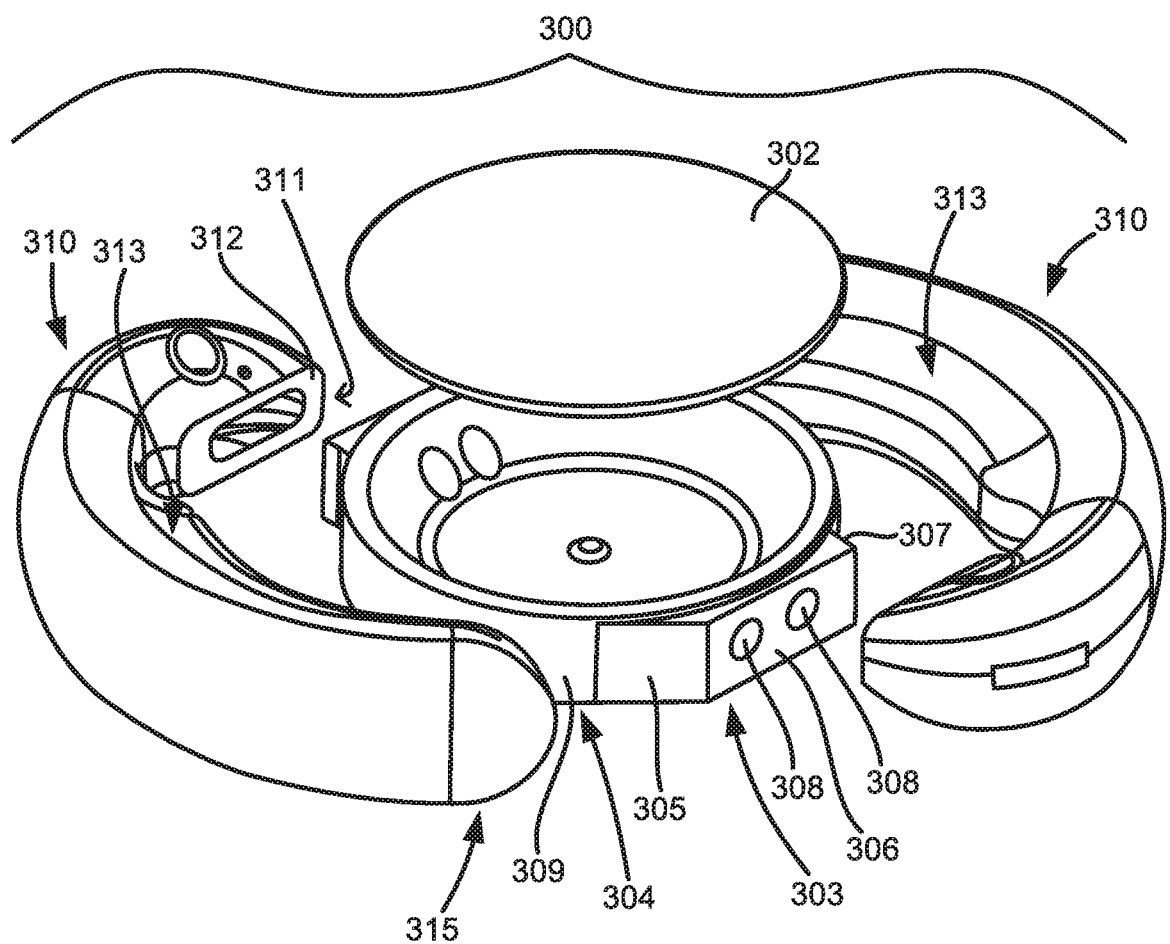
FIG. 16 shows an exemplary IOL.
Figure 17:
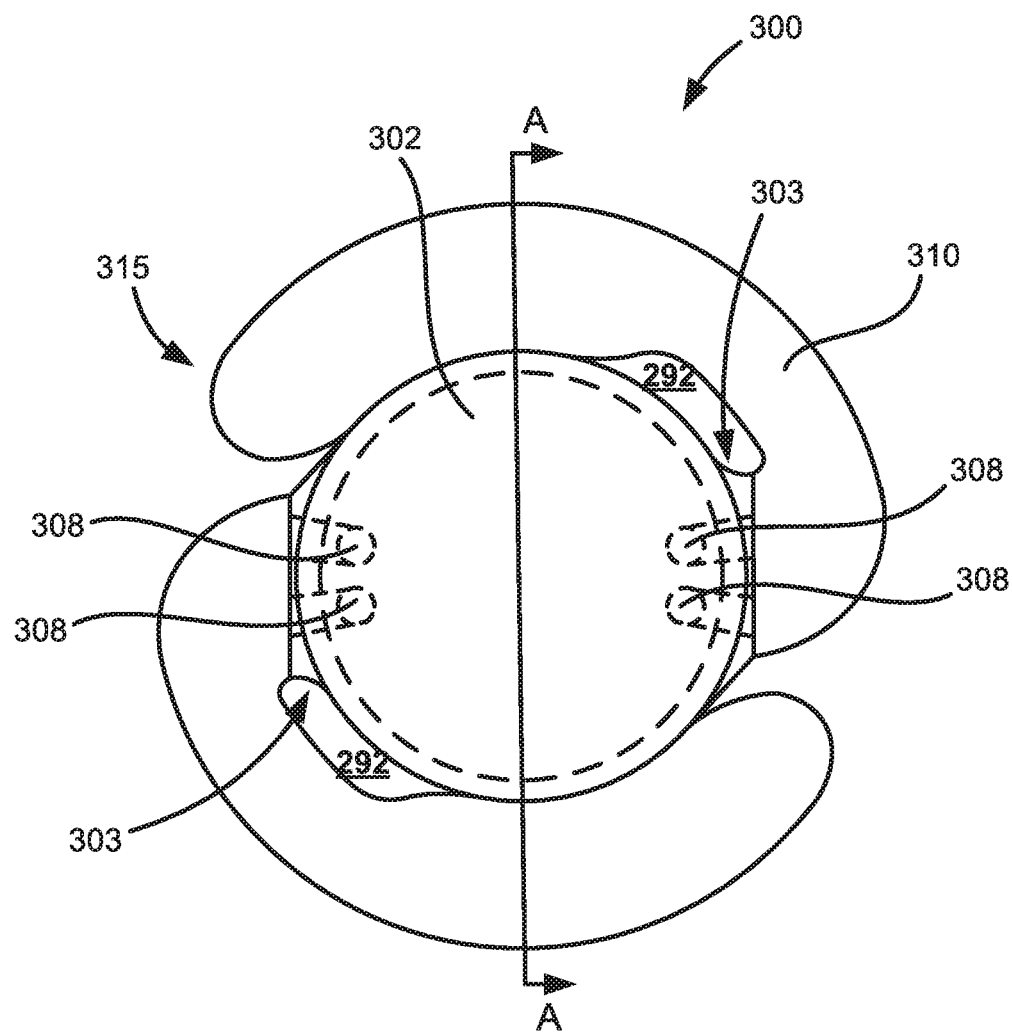
FIG. 17 shows a top view of an exemplary IOL.
Figure 18:
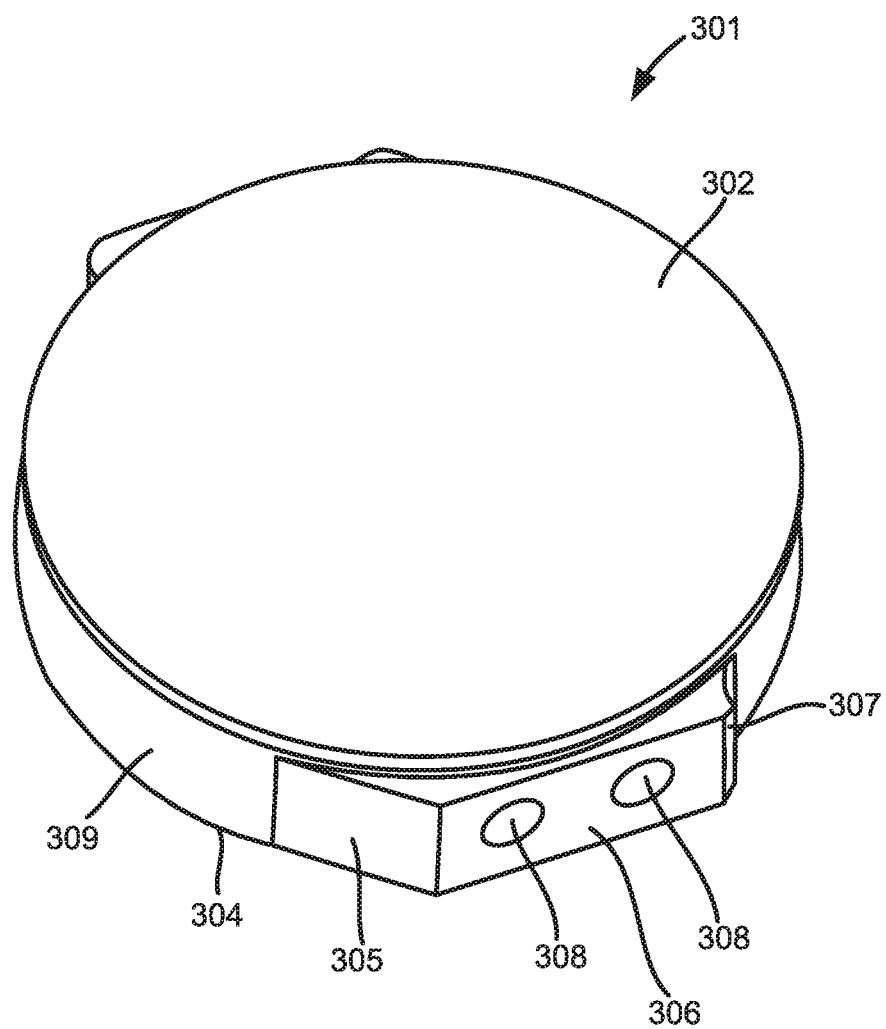
FIG. 18 shows an exemplary optic portion.
Figure 19:
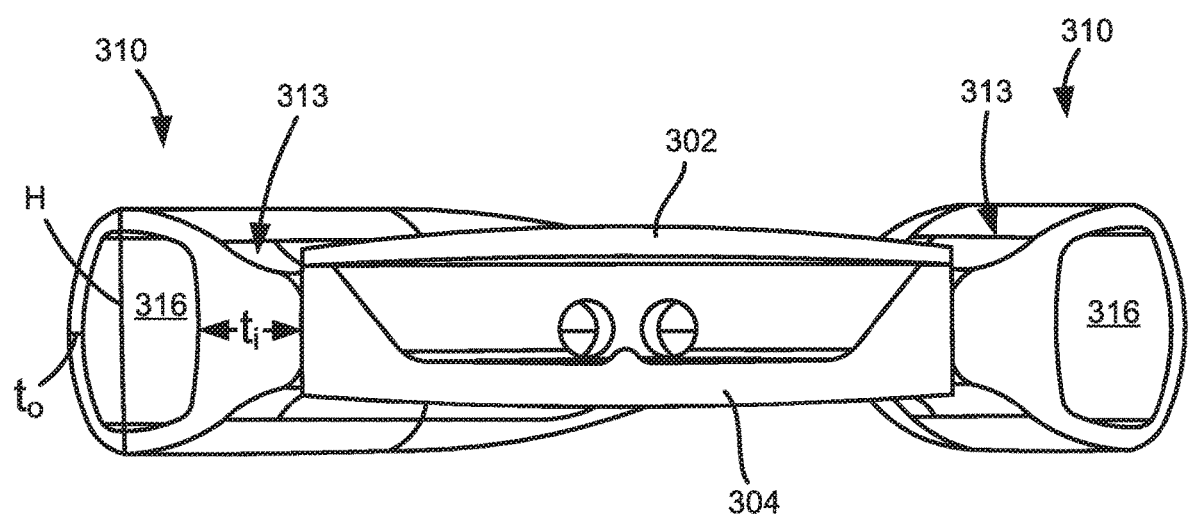
FIG. 19 shows a sectional view of an exemplary IOL.

In some embodiments in which one or more haptics are adhered to the optic body at discrete locations, rather than 180 degrees around the optic, a curing step that cures an adhesive that secures the haptic to the optic body may cause shrinkage of the material at the location where the two components are adhered. This shrinkage at the discrete locations can cause distortions in the lens, such as astigmatism. It can be beneficial, or necessary, to prevent or reduce the extent of the distortions. FIG. 16 illustrates an exploded perspective view of alternative accommodating intraocular lens 300. FIG. 17 illustrates a top view of AIOL 300. FIG. 18 illustrates a perspective view of option 301 of AIOL 300. FIG. 19 is a view of section A-A shown in FIG. 17.

FIGS. 16-18 illustrate an exemplary interface between an exemplary optic body 301 (see FIG. 18) and haptics 310 that may help alleviate distortions due to shrinkage at the location where the optic body and haptics are secured. The interface between the optic body 301 and the haptics 310 is relocated radially away from the optic body 301, and specifically the optical surfaces, compared to other embodiments such as in FIGS. 10-15. By moving the interface, and thus the location of potential shrinkage, away from the optical surfaces, the amount of distortion caused to the optical surfaces by the curing step can be reduced. A coupling region 311 of haptics 310 each interface with an optic projection 303, such that the interface between the haptics and the projection 303 is radially away from the optical surface of the optic. This type of interface can be used with non-accommodating or accommodating intraocular lenses, but in this embodiment the lens is an accommodating intraocular lens.

For example, the accommodating intraocular lens 300 can comprise the optic body 301 (see FIG. 18), and haptics 310. Is this embodiment, haptics 310 are manufactured separately from the optic 310, and then secured to the optic 310. The haptics 310 each include a radially inner flat surface 312 (only one labeled in FIG. 16) that is secured to a radially peripheral surface 306 of the optic 310. In this embodiment surface 312 is a radially inner surface of the coupling region 311 of haptic 310. For example, an adhesive can be used to secure surface 312 to the radially peripheral surface 306 of the optic 310. The process of securing the haptic to the optic may affect the optical performance of the optic 70, as discussed above. For example, the curing process of the adhesive may cause shrinkage of the optic 301 at two discrete locations, thus possibly resulting in distortion and aberration such as astigmatism of the intraocular lens.

In this embodiment, the intraocular lens comprises two projections 303 extending radially outwards away from a peripheral surface 309 of the posterior element 304 of optic 301. The projections 303 can be thought of as projections from the general curved periphery of the optic, as defined by outer edge surface 309. The haptics 310 can each have a first portion 311 secured to the projection 303 and a free second portion 315 disposed away from the first portion 311, wherein a radially inner surface of each of the haptics follows a radially outer peripheral surface of the optic. Projection 303 may also be referred to herein as a "landing" or "land" in this disclosure.

Projections 303 can be raised areas extending between 10 microns and 1 mm, optionally between 10 microns and 500 microns, radially outward from the periphery surface 309 of the optic. The radially peripheral surface 306 of the projections 303 can be between 10 microns and 1 mm, optionally between 10 microns and 500 microns, farther away radially from a center of the optic than the peripheral surface 309 of the optic. For example, projections 303 can be a raised area extending between 100 microns and 200 microns radially outward from the periphery surface 309 of the optic. The radially outer peripheral surface 305 of projection 303 may be between 100 microns and 200 microns farther away radially from a center of the optic than the peripheral surface 309 of the optic. Values outside the above range are also possible. Projections 303 can move the securing surfaces or coupling surfaces away from the optic to prevent optic disruption due to shrinkage when curing the adhesive between the optic and the haptic.

In some embodiments the optic has a circular shape, in a top view, and the radially outer peripheral edge 309 of the optic is generally circular. When the projections are described herein as extending radially away from the optic body, the projections may be extending away from the general curve of the radially outer peripheral edge of the optic.

In some embodiments, the optic and the projections 303 of the intraocular lens can be a single integral body. For example, projections 303 can be molded as part of the optic. In some other embodiments, projections 303 can be attached to the optic, such as by gluing.

In some embodiments the optic 301 comprises a posterior element and an anterior element, optionally defining a fluid chamber therebetween, such as in embodiments above. For example, projections 303 can be part of the posterior element because the posterior has a thicker periphery. The projections may also be part of the anterior element. For yet another example, the projections can be part of the posterior element and anterior element of the optic.

Outer surfaces 306 of projections 303 and inner surfaces 312 of haptics 310 can all be flat, such that they interface at a butt joint. For example, the radially outer peripheral surface 306 of projections 303 can comprise a flat surface, optionally entirely flat. The radially inner surface 312 of haptics 310 can comprise a flat surface as well, optionally entirely flat. For another example, the radially outer peripheral surface 306 of projections 303 can comprise a curved surface, optionally entirely curved. The radially inner surface 312 of haptics 310 can comprise a curved surface as well, optionally entirely curved. A curvature of radially outer peripheral surface 306 can be the same as the curvature of the periphery surface 309 of the optic body, and in some embodiments can be larger or smaller than the curvature of the periphery surface 309 of the optic body.

Haptics 310 can comprise a peripheral fluid chamber as described herein. The projections 303 can comprise at least one fluid channel 308, and optionally at least two channels, in fluid communication with the peripheral fluid chamber in the haptics. The raised projections 303 may provide more stability to the fluid channel because there is more optic material at the locations of the projections.

In general, the projection can be disposed on a non-accommodating (fixed power) intraocular lens that is manufactured by coupling haptics and optic as well. For example, a fixed power intraocular lens, where the intraocular lens is a non-fluid filled optic body with a single power (e.g., PMMA material) and two haptics, can comprise a projection extending radially outwards from a peripheral surface of the optic body as well.

The embodiment in FIGS. 16-19 also illustrate an alternative haptic cross sectional configuration (see FIG. 19 for the cross section) that can be incorporated into any of the suitable optics herein, such as optic 100 shown in FIG. 10. The height H (measured in anterior to posterior direction) of haptics 310 can be from 2 mm-2.5 mm, and may be 2.1 mm to 2.4 mm. This may be smaller than other haptic heights for other intraocular lenses, such as heights above 3 mm. It may be advantageous, but not necessarily necessary, to have heights between 2 and 2.5 mm for the haptics. There is some patient to patient variability in the size of the anatomy in the eye. There is variability in capsular size, for example, or distance between capsule and the posterior side of the iris. With some haptics, there may be some rubbing between the haptic and the posterior side of the iris. And even if there is, it may not raise any concerns. It may thus be advantageous, merely in an abundance of caution, to have haptics heights that minimize the chance of such rubbing.

Haptics 310 also include a radially inner wall portion 313 on the radially inner side of fluid chamber 316, which has a thickness "$t_i$" that is greater than a thickness "$t_o$" of the haptic wall on the radially outer side of chamber 316. In some embodiments "$t_i$" is between four and nine times greater than "$t_o$". Radially inner wall portion 313 may be referred to herein as a "spacer." As shown in FIG. 16, the spacer extends along almost the entire length of haptic, but does not exist where the spacing exists between the optic and haptic. The fluid chamber 316 radially inner wall is, as shown, flatter than fluid chamber 316 radially outer wall. Haptics 310 are examples of haptics that have a cross section, in a plane passing through an optical axis of the optic portion, in which the haptic fluid chamber is disposed in a radially outer portion of the haptic, and wherein a radially inner portion of the haptic is non-fluid. Haptics 310 are examples of haptics that, in a cross section of a plane passing through an optical axis of the optic portion, and in a direction orthogonal to an optical axis of the optic portion through a midpoint of the haptic, have a radially inner fluid chamber wall thickness that is between four and 10 times the thickness of a radially outer fluid chamber wall thickness. Haptics 310 are examples of haptics that, in a cross section of a plane passing through an optical axis of the optic portion, has an outer surface that is not symmetrical about any axis passing through the peripheral portion and parallel to an optical axis of the optic portion, and wherein the haptic has, in a direction orthogonal to an optical axis of the optic portion through a midpoint of the haptic has a radially inner fluid chamber wall thickness greater than a radially outer fluid chamber wall thickness. Haptics 310 are examples of haptics that, in a cross section of a plane passing through an optical axis of the optic portion, having a height dimension measured in an anterior to posterior direction, wherein the greatest height of the peripheral portion in a radially outer half of the peripheral portion is greater than the greatest height of the peripheral portion in a radially inner half of the peripheral portion.

In some embodiments one or more aspects of the optic body have a refractive index that is between about 1.48 and 1.55, such as between 1.50 and 1.53. In some embodiments the refractive index of one or components is about 1.48, about 1.49, about 1.50, about 1.51, about 1.52, about 1.53, about 1.54, or about 1.55. There may be a designed mismatch in refractive index between any of the anterior element, fluid, and posterior element, but in some embodiments there is a designed index matching between at least two of the components, and optionally all three. When all components of the optic are designed to have the same or substantially the same index of refraction, they are said to be index-matched. Any of the properties of the intraocular lenses (e.g., refractive index, fluid, monomer compositions) described in U.S. Prov. App. No. 62/173,877, filed Jun. 10, 2015 can be implemented in any of the intraocular lens designs herein.

Exemplary materials that can be used to make any of the IOLs, including fluid, herein, can be found in PCT/US2016/037055, fully incorporated by reference herein.

Peripheral portions with any configuration described herein can be coupled to the optic portion using any of the coupling concepts described herein. For example, peripheral portions with the configuration and cross sectional configurations shown in FIGS. 16 and 19 can be coupled to the optic portion even if the optic portion does not include a projection such as optic projection 303 shown in FIG. 16. For example, the haptics 310 shown in FIGS. 16 and 19 can be coupled to the optic portion using the coupling concepts and geometries shown in FIGS. 11-15. In such a scenario, the end of haptic 310 that is to be coupled to the optic would generally have a curved inner surface such as is shown in FIG. 13, such that a curved inner surface of the haptic would abut with the curved outer surface of the optic.

Intraocular lenses can be positioned into the eye (optionally into a capsular bag) using known techniques. During the surgical implantation procedure, at least a portion of the IOL may receive out of plane forces in the anterior-to-posterior direction. To help resist these forces and make it easier to achieve planar placement of the intraocular lens during at least a portion of the surgical procedure, the IOL can optionally include one or more additional features that help stabilize the peripheral portion relative to the optic portion in the anterior to posterior direction.

In some embodiments, at least a portion of the optic can have a configuration or shape that is complimentary to at least a portion of the peripheral portion. It can be an optic peripheral surface that is complimentary to at least a portion of an inner surface of the peripheral portion.

To optionally make it easier to achieve planar placement of the IOL during implantation (planar in this context referring to a plane orthogonal to an optical axis of the optic portion), the optic portion can optionally be adapted to increase the stability of the peripheral portion in the axial direction to try to prevent, minimize and/or reduce the axial movement of the peripheral portion relative to the optic portion.

Figure 20:
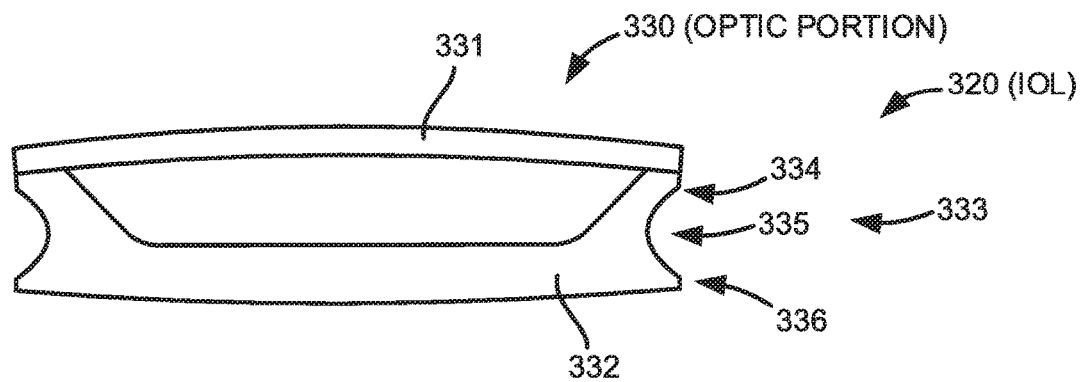
FIG. 20 is a sectional view of an exemplary optic that includes a peripheral surface.

FIG. 20 illustrates a sectional view of an optic portion of an exemplary intraocular lens 320 (optionally accommodating) that includes optic 330. The peripheral portion is not shown for clarity. Optic 330 includes anterior element 331 and posterior element 332, and unless indicated otherwise the intraocular lens can have (but not necessarily) features found in any of the embodiments in FIGS. 1A-19. The sectional view shown in FIG. 20 is the same sectional view taken along section A-A shown in FIG. 17. One difference between optic 330 and the optic in FIG. 19 is that optic 330 includes a peripheral surface 333 (in this embodiment a depression) along at least a portion of its periphery. A "depression" as used in this context generally refers to a surface of the periphery of the optic that extends radially inward than another portion of the optic periphery. In this example, peripheral surface 333 includes region 335 that is disposed further radially inward than optic region 334 and optic region 336. In this example, optic region 334 is anterior to depression region 335 and optic region 336 is posterior to depression region 335. The stability may be enhanced by having raised regions on both sides of the depression, but it is conceivable that in some embodiments the optic does not include regions both anterior and posterior to the depression that extend further radially outward that the depression, some examples of which are described below. For example, it may be desired to prevent movement of the peripheral portion in only one direction (e.g., anterior but not posterior, or posterior but not anterior).

The optic peripheral surface can have a variety of configurations, as long as it provides axial stability for the peripheral portion in at least one direction. The configuration of the peripheral surface may also depend on the peripheral portion configuration. In some embodiments the peripheral surface can have a general U-shape or a general C-shape (such as shown in FIG. 20), a scallop shape, etc. The peripheral surface configuration can include curved and/or flat surfaces. In some embodiments the optic peripheral surface includes one or two raised ridges that extend further radially outward than a region of the optic periphery disposed radially inward relative to the at least one raised ridge.

The peripheral surfaces as described herein can be thought of capturing at least a portion of the peripheral portion and reducing or minimizing movement of at least a portion of the peripheral portion in at least one of the anterior and posterior directions.

Figure 21:
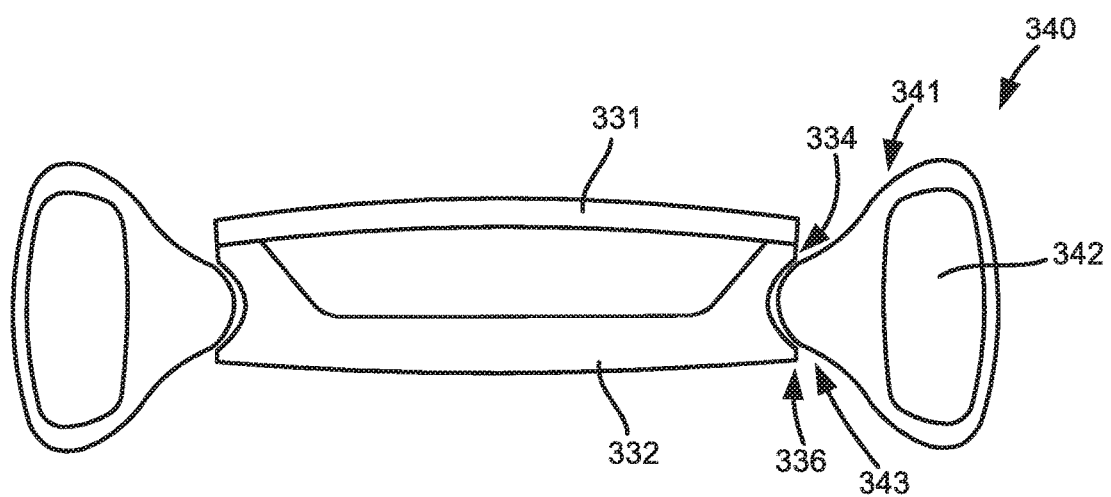
FIG. 21 is a sectional view of an exemplary AIOL that includes an optic with a peripheral surface and a peripheral portion two at least one radially inner surface.

FIG. 21 illustrates the same section A-A from FIG. 20, but includes peripheral portion 340, which in this embodiment includes first and second haptics, just as in the embodiment in FIG. 19. The haptics in FIG. 21 can be the same as in other regards, or similar to, the haptics in FIG. 19. The haptics include a body 341 that includes a portion 343 that extends further radially inward than a portion of the optic. In this embodiment haptic portion 343 extends further radially inward than optic region 334 and optic region 335, with region 334 being anterior to the haptic where the haptic extends further radially inward than region 334, and with region 336 being posterior to the haptic where the haptic extends further radially inward than region 336. In this embodiment the portion of the haptic that extends within the depression is a radially inner portion of the haptic.

Figure 22:
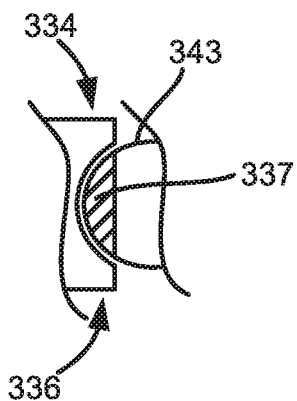
FIG. 22 is a close up sectional view of an exemplary optic peripheral surface and exemplary peripheral portion inner surface.

FIG. 22 illustrates a close-up view of only a portion of the intraocular lens, illustrating with a hypothetical dotted line and hashed marks the radially inner section 337 of a haptic that extends further radially inward than section 334 and 336 of the optic. It is this part 337 of the haptic that is considered to be radially within the optic peripheral surface.

In the embodiment in FIG. 21, only a portion of the haptic (measured along its height in the anterior-posterior direction), is disposed within the optic depression. In this embodiment a central region of the haptic is disposed adjacent to and within the depression, and regions of the haptic anterior and posterior to the central haptic region are not considered radially disposed within the depression. In some embodiments, 75% or less (measured along its height) of the peripheral portion is within the depression. In some embodiments 50% or less of the peripheral portion is within the depression, and in some embodiments, 25% or less of the peripheral portion is within the depression.

In the embodiment in FIG. 21, the portion of the peripheral portion that is within the optic depression does not extend directly from the optic. This means that this portion of the peripheral portion is not coupled to or integrally formed with the optic in this cross section. That is, the peripheral portion that is within the depression is spaced away from where the peripheral portion is extending from the optic (e.g., coupled to or integrally formed therewith). This helps clarify that the depression is, at least in this embodiment, not at the coupling location between the peripheral portion and the optic, but is disposed away from the coupling location. Section A-A from FIG. 17 (which is the same section as in FIGS. 19-21) is an example of a location that is spaced away from where the peripheral portions is extending directly from the optic.

In this embodiment, the portion of the haptic that is radially within the depression is directly adjacent to the optic (but not extending from the optic at that location), and in some instances can be engaging the optic or very nearly engaging the optic. In some embodiments the peripheral portion inner surface that is adjacent the optic is 100 microns or less away from the optic surface, and may be 50 microns or less away.

In an alternative to what is shown in FIG. 21, the depression can be solely in the anterior element (if the anterior element were thicker), or it can be formed in both the anterior and posterior elements.

In any of the accommodating intraocular lenses herein, the optic may not include separate anterior elements, and thus a depression as herein is not limited to being part of an anterior element or a posterior element (or both), but rather is considered part of the optic portion in general, regardless of the optic portion construction.

As set forth above, a depression can have a variety of configurations, and need not be symmetrical about an axis orthogonal to the optical axis of the optic. A depression may serve its purpose as long as it provides some axial stability to at least a portion of the peripheral portion. The configuration of the peripheral portion can therefore also influence the configuration of the periphery of the optic.

FIGS. 23-26 illustrate sectional views of alternative examples of optics with peripheral surfaces that include one or more depressions (they can be the same section A-A shown in FIG. 17). The optics in FIGS. 23-26 illustrate that optics other than those specifically described herein can include one or more depressions, and that the particular construction of the optic is not critical. The optics in FIGS. 23-26 are illustrated as monolithic structures to illustrate a variety of optics can have the depressions described herein. Additionally, any of the optics herein (including those in FIGS. 23-26) can be used with any of the peripheral portions herein (including any haptics herein). FIGS. 23-26 do not show the peripheral portion for clarity.

Figure 23:
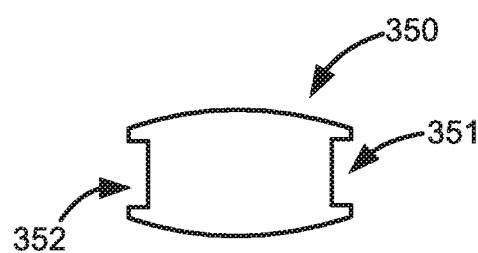
FIG. 23 illustrates an exemplary optic with a peripheral surface.

FIG. 23 illustrate optic portion 350 having first and second depressions 351 and 352, respectively, formed in the peripheral surface(s). In this embodiment the depressions have at least one flat surface.

Figure 24:
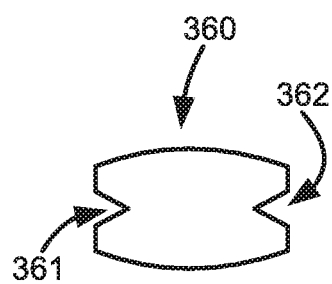
FIG. 24 illustrates an exemplary optic with a peripheral surface.

FIG. 24 illustrates optic 360 with peripheral surfaces that have depressions 361 and 362. Depressions 361 and 362 have flat surfaces, and generally define a valley.

Figure 25:
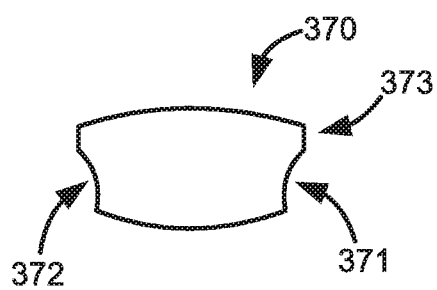
FIG. 25 illustrates an exemplary optic with a peripheral surface.

FIG. 25 illustrates optic 370, which includes peripheral surfaces that include depressions 371 and 372. In this embodiment, the depressions are not symmetrical about an axis orthogonal to the optical axis of the optic. In this embodiment, a portion 373 of the optic would be anterior to the haptic within the depression, but the optic does not have a portion posterior to the haptic within the depression. This might be used if only anterior movement of the peripheral portion were a concern. Similarly, the orientation of the optic could be flipped such that portion 373 is on the posterior side of the haptic within the depression.

Figure 26:
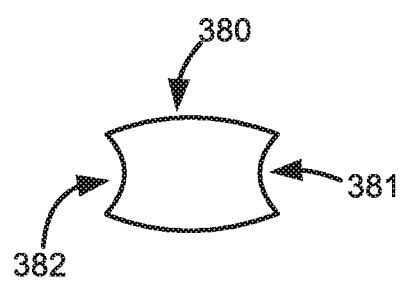
FIG. 26 illustrates an exemplary optic with a peripheral surface.

FIG. 26 includes optic 380, which includes peripheral surfaces that include depressions 381 and 382 that extend along all or substantially all of the periphery of the optic (in the anterior-posterior direction).

A peripheral surface (e.g., a depression) may extend around (in a top view such as in FIG. 17) any portion of the periphery of the optic or the entire periphery of the optic. A peripheral surface may in fact also extend around the region where the peripheral portion couples to the optic, but in general they do not.

In some embodiments, and in reference to FIG. 17, the optic comprises a peripheral surface (e.g., a depression) at least where a portion of the peripheral portion inner surface is directly adjacent to the optic. For example, in reference to FIG. 17, the depression could be present in the optic everywhere around the peripheral except at the coupling location and in the regions of spacings 292. In this embodiment, this is where the haptics are directly adjacent the optic and whose position can be stabilized due to its close proximity to the optic (which may in fact be toughing the optic). A depression could of course extend further than just those regions. For example, a depression could extend adjacent spacing 292, even if the depression in that area is not directly stabilizing a portion of the haptic. It may, for example, be easier to manufacture the depressions to be longer than needed.

In embodiments in which a depression does not extend around the entirety of the optic, there can thus be more than one depression separated by a region of the optic that does not include a depression. They can be any number of separate depressions as desired.

There may be peripheral portions that are more annular than the peripheral portions herein, and may in fact completely surround the optic. Depressions in these embodiments may extend around a substantial portion of the optic.

In any of the embodiments herein, the peripheral portion can alternatively have any of the depressions herein in the radially inner surface, and the peripheral surface of the optic can have a shape (e.g., radial extension outward), at least a portion of which is complementary to the peripheral portion depression. All other aspects of the disclosure can apply to these alternative embodiments.

Any of the depressions herein can be created during manufacturing one or more components of the intraocular lens, such as during machining or molding of one or more parts.

Any of the different ways of incorporating at least one depression can be incorporated into any of the different embodiments herein.

In some embodiments herein the surface is described an a depression, but it is understood that a depression is just an exemplary peripheral surface (if part of the optic) and an exemplary radially inner surface (if part of the peripheral portion) and not intended to be limiting.

The embodiments in all of FIGS. 20-26 are examples of an outer periphery of an optic portion that has a peripheral surface that is at least partially complimentary in shape to at least a portion of a radially inner portion of a peripheral portion of the IOL, wherein the optic surface is directly adjacent to the radially inner portion, and wherein the optic surface does not directly extend (coupled to or integrally formed therewith) from the radially inner portion where they are directly adjacent.

The embodiments in all of FIGS. 20-26 are examples of an intraocular lens, wherein an outer periphery of an optic portion has a peripheral surface, and a radially inner portion of a peripheral portion of the IOL has a radially inner surface, wherein the peripheral surface is directly adjacent to the inner surface, and wherein the peripheral surface does not directly extend (coupled to or integrally formed therewith) from the inner surface, and wherein the peripheral surface and the inner surface are configured so that the peripheral portion is stabilized in at least one of, and optionally both of, the proximal and distal directions relative to the optic portion.

What is claimed is:

1. A fluid-filled intraocular lens (IOL), comprising:
an optic portion comprising an optic fluid chamber; and
a peripheral portion comprising at least one peripheral fluid chamber in fluid communication with the optic fluid chamber,
wherein an outer periphery of the optic portion has a peripheral surface, wherein a radially inner portion of the peripheral portion of the IOL has an inner surface,
wherein the peripheral surface comprises a depression, wherein the depression is defined such that a portion of the peripheral surface is set radially inward relative to another portion of the peripheral surface along an anterior-to-posterior direction, wherein at least a portion of the inner surface is disposed in the depression,
wherein the peripheral surface is directly adjacent to the inner surface, and wherein the peripheral surface does not directly extend from the inner surface, and
wherein the peripheral surface and the inner surface are both configured so that the peripheral portion and the optic portion are stabilized, relative to one another, in at least one of an anterior direction and a posterior direction when the peripheral surface is directly adjacent to the inner surface.

2. The intraocular lens of claim 1, wherein the inner surface that is disposed in the depression is disposed axially between an anterior-most location of the optic portion and a posterior-most location of the optic portion.

3. The intraocular lens of claim 1, wherein the inner surface is spaced away from and around the outer periphery of the optic portion from a location where the peripheral portion extends from the optic portion.

4. The intraocular lens of claim 1, wherein the inner surface is disposed between a location where the peripheral portion extends from the optic portion and a free and closed distal end of the peripheral portion.

5. The intraocular lens of claim 1, wherein the inner surface of the peripheral portion is physically engaging the optic portion or directly adjacent to the optic portion, and not directly physically attached to the optic portion where they are physically engaged or directly adjacent.

6. The intraocular lens of claim 1, wherein a midpoint of the peripheral portion, measured in an anterior-to-posterior direction, is part of the inner surface that is disposed in the depression of the optic portion.

7. The intraocular lens of claim 1, wherein the depression is symmetrical about an axis orthogonal to an optical axis of the optic portion.

8. The intraocular lens of claim 1, wherein the inner surface of the peripheral portion disposed in the depression is symmetrical about an axis orthogonal to an optical axis of the optic portion.

9. The intraocular lens of claim 1, wherein the depression is disposed axially in an anterior-to-posterior direction between an anterior most location of the optic portion and a posterior most location of the optic portion.

10. The intraocular lens of claim 1, wherein the inner surface that is disposed in the depression has a height in an anterior-to-posterior direction that is less than a greatest height dimension of the peripheral portion.

11. The intraocular lens of claim 1, wherein the peripheral portion is coupled to the optic portion at one or more coupling locations, and wherein the peripheral portion extends around the outer periphery of the optic portion.

12. The intraocular lens of claim 1, wherein the peripheral portion comprises at least a first haptic, the first haptic coupled to the optic portion at a coupling location, wherein the first haptic extends partially around the outer periphery of the optic portion, wherein a free end of the first haptic is not directly attached to the optic portion, and wherein the radially inner portion is an inner portion of the first haptic.

13. The intraocular lens of claim 12, wherein the peripheral portion comprises a second haptic, wherein the second haptic is coupled to the optic portion at a second coupling location, wherein the second haptic partially extends around the outer periphery of the optic portion, and wherein a second free end of the second haptic is not directly attached to the optic portion.

14. The intraocular lens of claim 1, wherein the depression does not extend circumferentially along the outer periphery to a location where the peripheral portion extends from the optic portion.

15. The intraocular lens of claim 1, wherein at least part of the inner surface is disposed in the depression of the optic portion.

16. A fluid-filled intraocular lens, comprising:
an optic portion comprising an optic fluid chamber; and
a peripheral portion comprising at least one peripheral fluid chamber in fluid communication with the optic fluid chamber,
wherein an outer periphery of the optic portion has a peripheral surface that is complementary in shape to at least a portion of a radially inner portion of the peripheral portion of the intraocular lens such that the peripheral surface is defined by a concavity and the radially inner portion is defined by a protrusion complementary in shape to the concavity, and
wherein the peripheral surface does not directly extend from the radially inner portion where they are directly adjacent.

17. The intraocular lens of claim 16, wherein the peripheral surface comprises a depression, wherein the depression is defined such that a portion of the peripheral surface is set radially inward relative to another portion of the peripheral surface along an anterior-to-posterior direction.

18. The intraocular lens of claim 16, wherein the peripheral portion is coupled to the optic portion at one or more coupling locations, and wherein the peripheral portion extends around the outer periphery of the optic portion.

19. The intraocular lens of claim 16, wherein the peripheral portion comprises at least a first haptic, the first haptic coupled to the optic portion at a coupling location, wherein the first haptic extends partially around the outer periphery of the optic portion, wherein a free end of the first haptic is not directly attached to the optic portion, and wherein the radially inner portion is an inner portion of the first haptic.

20. The intraocular lens of claim 19, wherein the peripheral portion comprises a second haptic, wherein the second haptic is coupled to the optic portion at a second coupling location, wherein the second haptic partially extends around the outer periphery of the optic portion, and wherein a second free end of the second haptic is not directly attached to the optic portion.

* * * * *